(12) United States Patent
Guo et al.

(10) Patent No.: US 10,845,303 B2
(45) Date of Patent: Nov. 24, 2020

(54) APPARATUS, SYSTEM AND METHOD FOR GAS DETECTION, AND APPARATUS MANUFACTURING METHOD

(71) Applicant: JINAN UNIVERSITY, Guangzhou (CN)

(72) Inventors: Tuan Guo, Guangzhou (CN); Christophe Caucheteur, Guangzhou (CN); Fu Liu, Guangzhou (CN); Xuejun Zhang, Guangzhou (CN); Shunshuo Cai, Guangzhou (CN)

(73) Assignee: JINAN UNIVERSITY, Guangzhou (CN)

( * ) Notice: Subject to any disclaimer, the term of this patent is extended or adjusted under 35 U.S.C. 154(b) by 0 days.

(21) Appl. No.: 16/897,930

(22) Filed: Jun. 10, 2020

(65) Prior Publication Data

US 2020/0326278 A1 Oct. 15, 2020

Related U.S. Application Data

(63) Continuation-in-part of application No. 16/382,186, filed on Apr. 11, 2019, now Pat. No. 10,718,711.

(51) Int. Cl.
| | |
|---|---|
| *G01J 4/00* | (2006.01) |
| *G01N 21/39* | (2006.01) |
| *G02B 6/02* | (2006.01) |
| *G01N 33/00* | (2006.01) |
| *G01N 21/552* | (2014.01) |
| *G01N 31/22* | (2006.01) |

(52) U.S. Cl.
CPC ........... *G01N 21/39* (2013.01); *G01N 21/554* (2013.01); *G01N 31/223* (2013.01); *G01N 33/004* (2013.01); *G01N 33/005* (2013.01); *G01N 33/0037* (2013.01); *G01N 33/0044* (2013.01); *G01N 33/0047* (2013.01); *G02B 6/02085* (2013.01); *G01N 2201/0635* (2013.01); *G01N 2201/0636* (2013.01)

(58) Field of Classification Search
CPC .............. G01N 21/211; G01N 21/21; G01N 2021/213; G01J 4/00; G01B 11/0641
USPC ........................................................ 356/369
See application file for complete search history.

(56) References Cited

U.S. PATENT DOCUMENTS

| | | | |
|---|---|---|---|
| 2006/0119853 A1* | 6/2006 | Baumberg | G01N 21/658 |
| | | | 356/445 |
| 2008/0007732 A1* | 1/2008 | Ja | G01N 21/6428 |
| | | | 356/445 |

* cited by examiner

*Primary Examiner* — MD M Rahman
(74) *Attorney, Agent, or Firm* — Pattao, LLC; Junjie Feng

(57) ABSTRACT

A sensing apparatus for detecting at least one target molecule in a gaseous medium is provided, comprising an optical fiber having a core with a tilted grating, and a coating assembly. The coating assembly has a composite film layer having an outer surface in direct contact with the gaseous medium, and contains at least two compositions mixed with one another therein, which include one or more surface plasmon resonance (SPR)-active compositions and one or more reacting compositions that are reversibly reactive to the at least one target molecule. Depending on different reacting compositions, the sensing apparatus can detect various target gas molecules such as hydrogen, ammonia, methane, and formaldehyde, etc. The sensing apparatus has relatively fast response time and high resistance to deactivation. A sensing system based on the sensing apparatus, a manufacturing method of the sensing apparatus, and a detection method using the sensing system, are further provided.

20 Claims, 16 Drawing Sheets

APPARATUS, SYSTEM AND METHOD FOR GAS DETECTION, AND APPARATUS MANUFACTURING METHOD

CROSS-REFERENCE TO RELATED APPLICATION

The present application is a continuation-in-part application of U.S. patent application Ser. No. 16/382,186 filed on Apr. 11, 2019, the disclosure of which is hereby incorporated by reference in its entirety.

TECHNICAL FIELD

This present disclosure relates generally to the field of chemical sensing technologies, and specifically to a fiber optical sensing apparatus for detecting a target molecule in a gaseous medium, such as hydrogen ($H_2$) in the air.

BACKGROUND

As a high energy-density, carbon-free, renewable and zero-pollution energy carrier, hydrogen ($H_2$) is a promising green energy source, but it also represents a highly flammable and explosive gas at concentrations ranging from 4%-75% in the air. For safety reasons, any leaks in hydrogen energy storage systems, vehicles, and appliances, as well as the entire hydrogen distribution infrastructure, must be detected immediately.

U.S. patent application Ser. No. 16/382,186 discloses a fiber optical sensor capable of sensitively detecting target molecules in a gaseous medium having a refractory index of around 1.0, such as the air, and embodiments also disclosed therein include sensors that can detect hydrogen ($H_2$) at a high sensitivity (such as <50 ppm) in the air. The optical fiber hydrogen sensor disclosed therein either has a single-layer structure comprising a palladium (Pd) thin film or has a double-layer structure comprising a hydrogen-reacting palladium (Pd) thin film over a substrate layer of a surface plasmon resonance (SPR)-active thin film of gold (Au) or silver (Ag), which has advantages such as corrosion resistance, suitability for remote sensing, and more importantly, high level of safety due to the fact that the optical signals in the fiber optical hydrogen sensor generates no sparks as opposed to electrical signals.

Notably, the sensing function of the optical fiber hydrogen sensor stems from the absorption of hydrogen species into interstitial sites of the metal host, i.e. palladium (Pd), which renders such sensors intrinsically highly hydrogen-selective. This is because Pd undergoes a reversible phase transition from metal to metal hydride when hydrogen is captured within the Pd crystal lattice at room temperature, which consequently modifies the optical properties and effectively modulates the optical and dielectric constants. Yet optical fiber hydrogen sensor has relatively long response time (e.g. in the order of 100 s) and long recovery time (e.g. 400 s).

SUMMARY

One purpose of this disclosure is to improve the design of the inventions disclosed in the U.S. patent application Ser. No. 16/382,186 by disclosing a gas sensing apparatus, system and method that has a relatively faster response time and an improved deactivation resistance.

In a first aspect, a sensing apparatus for selectively detecting at least one target molecule in a gaseous medium is disclosed, which includes an optical fiber and a coating assembly coating an outer surface of the optical fiber.

The optical fiber includes a core and a cladding surrounding the core. The core is provided with a tilted grating, configured to generate surface plasmon waves at an interface between the coating assembly and the gaseous medium upon a compatible electromagnetic radiation propagating in the optical fiber.

The coating assembly comprises a composite film layer having an outer surface in direct contact with the gaseous medium, and the composite film layer comprises at least two compositions mixed with one another therein. The at least two compositions comprise one or more active compositions, each configured to be active to surface plasmon resonance (SPR); and the at least two compositions comprise one or more reacting compositions, each configured to be reversibly reactive to one or more of the at least one target molecule.

Herein, the one or more active compositions in the composite film layer can contain at least one of gold (Au), silver (Ag), platinum (Pt), aluminum (Al), or copper (Cu).

According to different embodiments of the sensing apparatus disclosed herein, the one or more reacting compositions in the composite film layer comprise at least one of palladium (Pd), metallic La—$Mg_2$—Ni, tungsten trioxide ($WO_3$), carbon nanotubes (CNT), Si nanowires, tin dioxide ($SnO_2$), a metal-polymer hybrid nanomaterial, a semiconductor oxide nanostructure, a core/shell plasmonic nanorod metamaterial, zinc oxide (ZnO), titanium oxide ($TiO_2$), iron oxide ($Fe_2O_3/Fe_3O_4$), polyaniline, polypyrrole, metal phthalocyanine, graphite oxide, or copper (II) oxide (CuO).

According to certain embodiments, the sensing apparatus can be configured to selectively detect hydrogen ($H_2$), and the one or more reacting compositions in the composite film layer comprise at least one of palladium (Pd), metallic La—$Mg_2$—Ni, Si nanowires, a metal-polymer hybrid nanomaterial, a semiconductor oxide nanostructure, a core/shell plasmonic nanorod metamaterial.

Further optionally, in the above hydrogen sensing apparatus, the one or more reacting compositions can comprise palladium (Pd), which has a weight concentration of approximately 20%-80% in the composite film layer. Furthermore, in the sensing apparatus described above, the one or more active compositions in the composite film layer comprise gold (Au).

According to some embodiments of the sensing apparatus, the one or more reacting compositions comprise $WO_3$, and the at least one target molecule comprises at least one of hydrogen ($H_2$), $H_2S$, or ammonia ($NH_3$).

According to some other embodiments of the sensing apparatus, the one or more reacting compositions comprise $SnO_2$, and the at least one target molecule comprises at least one of hydrogen ($H_2$), $CH_4$, formaldehyde, benzene, or ammonia ($NH_3$).

According to yet some other embodiments of the sensing apparatus, the one or more reacting compositions comprise CuO, and the at least one target molecule comprises $NO_2$.

According to yet some other embodiments of the sensing apparatus, the one or more reacting compositions comprise $TiO_2$, and the at least one target molecule comprises at least one of CO or ammonia ($NH_3$).

According to yet some other embodiments of the sensing apparatus, the one or more reacting compositions comprise ZnO, and the at least one target molecule comprises at least one of NO, formaldehyde, or ammonia ($NH_3$).

According to yet some other embodiments of the sensing apparatus, the one or more reacting compositions comprise carbon nanotubes, and the at least one target molecule comprises hydrogen ($H_2$) or benzene.

According to yet some other embodiments of the sensing apparatus, the one or more reacting compositions comprise at least one of iron oxide ($Fe_2O_3/Fe_3O_4$), polyaniline, polypyrrole, or metal phthalocyanines, and the at least one target molecule comprises ammonia ($NH_3$).

In any of the embodiments of the sensing apparatus described above, the composite film layer can optionally have a thickness in range of approximately 25-75 nm, and an internal tilt angle of the tilted grating can be at least approximately 20 degrees.

According to some embodiments of the sensing apparatus, the coating assembly further comprises a transition layer, which is sandwiched between the outer surface of the optical fiber and an inner surface of the composite film layer, and is configured to improve adhesion of the composite film layer to the optical fiber. The transition layer can optionally comprise at least one of titanium (Ti), molybdenum (Mo), or chromium (Cr).

According to some embodiments of the sensing apparatus, the coating assembly further comprises a substrate layer, which is sandwiched between the outer surface of the optical fiber and an inner surface of the composite film layer, and is configured to be active to SPR. The substrate layer optionally can comprise at least one of gold (Au), silver (Ag), platinum (Pt), aluminum (Al), or copper (Cu). Herein, optionally, the coating assembly can further include a transition layer, which is sandwiched between the outer surface of the optical fiber and an inner surface of the substrate layer, and is configured to improve adhesion of the substrate layer to the optical fiber, and the transition layer can comprise at least one of titanium (Ti), molybdenum (Mo), or chromium (Cr).

In a second aspect, a sensing system comprising the sensing apparatus as disclosed above in the first aspect is further provided.

The sensing system further includes a light source apparatus, which is optically coupled to a first end of, and is configured to provide an input light into, the sensing apparatus so as to allow the electromagnetic radiation to propagate in the core of the optical fiber of the sensing apparatus. The sensing system further includes a signal detection apparatus, which is coupled to the sensing apparatus and is configured to obtain the signals of the surface plasmon waves therefrom so as to derive the information of the at least one target molecule in the gaseous medium.

According to some embodiments of the sensing system, the light source apparatus comprises a broadband source (BBS), and the signal detection apparatus comprises an optical spectrum analyzer (OSA).

According to some other embodiments of the sensing system, the light source comprises a tunable laser source (TLS). The signal detection apparatus comprises an optical detector, which is configured to detect, and to convert into analog electrical signals, the signals of the plasmon waves from the sensing apparatus. The signal detection apparatus further includes an analog-to-digital converter, which is configured to convert the analog electrical signals into digital electrical signals.

According to yet some other embodiments of the sensing system, the signal detection apparatus is coupled to the first end of the optical fiber, and a second end of the optical fiber is provided with a mirror having a reflection surface facing to, configured to reflect the electromagnetic radiation back towards, the first end of the optical fiber. The sensing system further comprises a coupler, which is arranged between the light source apparatus and the sensing apparatus along an input optical pathway and between the sensing apparatus and the signal detection apparatus along an output optical pathway. The coupler is configured to separate the input optical pathway and the output optical pathway to thereby allow the signal detection apparatus to obtain the signals of the surface plasmon waves from the sensing apparatus without being influenced by the input light.

In a third aspect, the present disclosure further provides a method for manufacturing the sensing apparatus as described above in the first aspect. The manufacturing method comprises the following steps:

(1) providing an optical fiber. Herein, the optical fiber includes a core and a cladding surrounding the core, and the core is provided with a tilted grating, which is configured to generate surface plasmon waves at an interface between the coating assembly and the gaseous medium upon a compatible electromagnetic radiation propagating in the optical fiber; and (2) coating a composite film layer over an outer surface of the optical fiber. Herein, the composite film layer comprises at least two compositions mixed with one another therein, and the at least two compositions comprise one or more active compositions and one or more reacting compositions. Each active composition is configured to be active to surface plasmon resonance (SPR); and each reacting composition is configured to be reversibly reactive to one or more of the at least one target molecule.

According to different embodiments of the disclosure, the step of coating a composite film layer over an outer surface of the optical fiber can be realized by means of sputtering, electroplating, or chemical deposition.

In the embodiments of the manufacturing method where the step of coating a composite film layer over an outer surface of the optical fiber is realized by means of sputtering, the step of coating a composite film layer over an outer surface of the optical fiber can include a sub-step of simultaneously sputtering the at least two compositions to the optical fiber while the optical fiber is rotating about an axis thereof.

Furthermore, in the above sputtering-based manufacturing method, each of the at least two compositions in the composite film layer is a metal, and the simultaneously sputtering the at least two compositions to the optical fiber is by means of a single common radio-frequency power source. Non-limiting examples include the manufacturing of the sensing apparatus having Pd and Au as compositions in the composite film layer.

According to some embodiments, the method further includes a step between the step of providing an optical fiber and the step of coating a composite film layer over an outer surface of the optical fiber. The step includes: coating a transition layer over an outer surface of the optical fiber. Herein the step of coating a composite film layer over an outer surface of the optical fiber comprises: coating a composite film layer over an outer surface of the transition layer.

In a fourth aspect, a method for selectively detecting a target molecule in a medium utilizing the aforementioned sensing system is further provided. The method comprises:

providing a sensing system;

arranging the sensing apparatus such that the coating assembly thereof exposes to the medium;

switching on the light source apparatus to provide an input light into the sensing apparatus;

obtaining, by means of the signal detection apparatus, signals of surface plasmon waves produced on the interface between the coating assembly and the medium upon excitement by the input light; and analyzing the signals of the surface plasmon waves to thereby derive the information of the target molecule in the medium.

According to some embodiments, the step of obtaining, by means of the signal detection apparatus, signals of surface plasmon waves produced on the interface between the coating assembly and the medium upon excitement by the input light comprises: obtaining, by means of the signal detection apparatus, signals of the surface plasmon waves and signals of other optical waves in the core. The step of analyzing the signals of the surface plasmon waves to thereby derive the information of the target molecule in the medium comprises: analyzing the signals of the surface plasmon waves and the signals of the other optical waves to thereby derive the information of the target molecule in the medium.

According to some embodiments, the light source apparatus comprises a broadband source (BBS), and the signal detection apparatus comprises an optical spectrum analyzer (OSA). As such, in the method, the step of switching on the light source apparatus to provide an input light into the sensing apparatus comprises: switching on the broadband source (BBS) to provide an input light with a broadband into the sensing apparatus. Correspondingly, the step of analyzing the signals of the surface plasmon waves comprises: performing a spectral interrogation over the signals of the surface plasmon waves to quantify a wavelength shift and optical intensity change induced by a refractive index change of the sensing apparatus so as to derive information of the target molecule in the gaseous medium.

According to some embodiments of the method, in the step of providing a sensing system, the sensing apparatus is determined to have a first wavelength of light that, upon being inputted into the sensing apparatus, produces a most sensitive mode of the plasmon waves, the light source apparatus comprises a tunable laser (TLS), and the signal detection apparatus comprises an optical detector and an analog-to-digital converter. As such, the step of switching on the light source apparatus to provide an input light into the sensing apparatus comprises: switching on the tunable laser (TLS) such that an input light having a second wavelength matching the first wavelength is produced and emits into the sensing apparatus. The step of obtaining, by means of the signal detection apparatus, signals of surface plasmon waves comprises the sub-steps of converting, by means of the optical detector, the signals of the surface plasmon waves from the sensing apparatus into analog electrical signals; and converting, by means of the analog-to-digital converter, the analog electrical signals into digital electrical signals. The step of analyzing the signals of the surface plasmon waves to thereby derive the information of the target molecule in the medium comprises: performing an interrogation over a quantification of intensity variations to thereby derive the information of the target molecule in the medium based on the digital electrical signals.

According to some embodiments, the sensing system comprises more than one sensing apparatus, optically connected to one another in series and each comprising an optical fiber sharing a common electromagnetic radiation propagation pathway. As such, in the method, the step of obtaining, by means of the signal detection apparatus, signals of surface plasmon waves produced on the interface between the coating assembly and the medium upon excitement by the input light comprises: differentially obtaining, by means of the signal detection apparatus, signals of surface plasmon waves from each of the more than one sensing apparatus. The step of analyzing the signals of the surface plasmon waves comprises: differentially analyzing the signals of the surface plasmon waves from the each of the more than one sensing apparatus.

DETAILED DESCRIPTION OF THE INVENTION

Figure 1A:
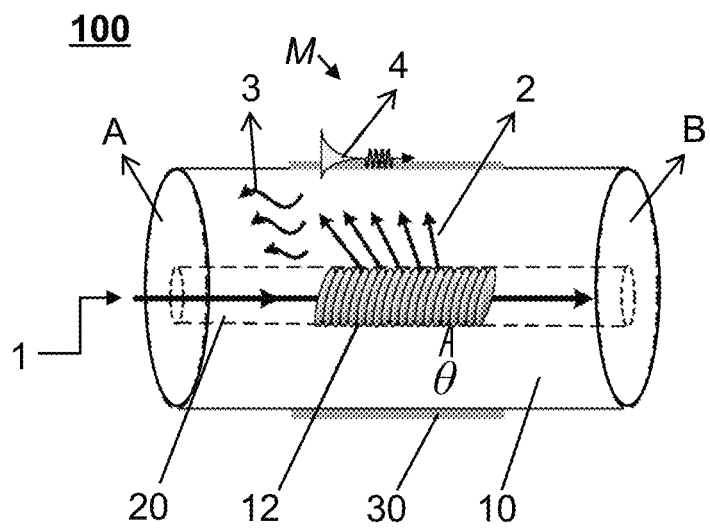
FIGS. 1A and 1B are respectively a perspective view and a cross-sectional view of a sensing apparatus according to some embodiments of the disclosure.

In a first aspect, the present disclosure provides an optical fiber-based sensing apparatus that is capable of selectively and sensitively detecting a target molecule in a gaseous medium at a relatively fast response time and recovery time, and exhibits a relatively high resistance to deactivation and poisoning. Non-limiting examples of the target molecules that can be detected by the sensing apparatus disclosed herein can include hydrogen ($H_2$), ammonia ($NH_3$), methane ($CH_4$), hydrogen sulfide ($H_2S$), carbon monoxide (CO), nitrogen dioxide ($NO_2$), nitric oxide (NO), formaldehyde ($CH_2O$), benzene ($C_6H_6$), etc. The gaseous medium can be air, or can be a mixture or combination of multiple gases.

The sensing apparatus comprises an optical fiber and a coating assembly coating an outer surface thereof. The optical fiber comprises a core and a cladding surrounding the core, wherein the core is provided with a tilted grating. The coating assembly is configured to be active to surface plasmon resonance (SPR), and is further configured to be reversibly reactive to the target molecule to allow for repeated detection with high reproducibility. The sensing apparatus is configured, primarily through appropriate configurations of the tilted grating (e.g. having an appropriate internal tilted angle, period, and pitch, etc.) and the coating assembly (e.g. having an appropriate composition, thickness, and configuration, etc.), such that upon a compatible electromagnetic radiation propagating in the optical fiber, surface plasmon waves can be generated at an interface between the coating assembly and the gaseous medium, whereas signals of the surface plasmon waves contain information of, and can be analyzed to characterize, the target molecule in the gaseous medium.

In the sensing apparatus disclosed herein, the coating assembly substantially comprises a composite film layer, which has an outer surface that is in direct contact with the gaseous medium and thus substantially represents a target molecule-reacting layer. The composite film layer further comprises at least two compositions that are mixed with one another therein.

Among the at least two compositions in the composite film layer, there are one or more active compositions, each of which is configured to be active to surface plasmon resonance (SPR). An SPR-active composition can be a composition with free electrons available for coupling into surface plasmon waves propagating along the surface of the material. Non-limiting examples of an SPR active composition include: a single material such as a metal (e.g. gold (Au), silver (Ag), platinum (Pt), aluminum (Al), or copper (Cu)), or a conducting metal oxide (e.g. indium tin oxide (ITO)), but can also comprise a semiconductor material, a dielectric material, or a two-dimensional material. According to certain embodiments, there is only one such SPR-active composition in the composite film layer. According to some other embodiments, there can be a combination of multiple such SPR-active materials/substances, such as an alloy formed among Au or Ag, and so on.

Further among the at least two compositions in the composite film layer, there are also one or more reacting compositions, each of which is configured to be reversibly reactive to the target molecule. The one or more reacting compositions can be selected based on their respective reactivity with the target molecule to be detected. Depending on different target molecules, a corresponding reacting composition that can selectively detect the target molecule can be chosen in different embodiments of the sensing apparatus. The possible pairs of the target molecule and its corresponding reacting composition(s) are listed in Table 1.

TABLE 1

Target molecule-reacting composition pairs

| Target molecule | Reacting composition(s) |
| --- | --- |
| hydrogen ($H_2$) | palladium (Pd), metallic La-$Mg_2$-Ni, tungsten trioxide ($WO_3$), carbon nanotubes (CNT), Si nanowires tin dioxide ($SnO_2$), Metal-polymer hybrid nanomaterials, semiconductor oxide nanostructures, or core/shell plasmonic nanorod metamaterials |
| ammonia ($NH_3$) | tin oxide ($SnO_2$), zinc oxide (ZnO), tungsten oxide ($WO_3$), titanium oxide ($TiO_2$), iron oxide ($Fe_2O_3/Fe_3O_4$), polyaniline, polypyrrole, metal phthalocyanines, or graphite oxide |
| hydrogen sulfide ($H_2S$) | tungsten oxide ($WO_3$) (Shujah T and Ikram M, et al. 2019; Singh S and Dogra N, et al. 2020; Yin L and Qu P, et al. 2019) |
| methane ($CH_4$) | tin oxide ($SnO_2$) (Bunpang K and Wisitsoraat A, et al. 2019; Das A and Panda D, 2019) |
| nitrogen dioxide ($NO_2$) | copper (II) oxide (CuO) (Navale YH and Navale ST, et al. 2019; Cai G and Duan P, et al. 2019) |
| carbon monoxide (CO) | titanium oxide ($TiO_2$) (Zhang L and Cheng X, et al. 2020; Chachuli SAM and Hamidon MN, et al. 2020) |
| nitric oxide (NO) | zinc oxide (ZnO) (Chinh ND and Hien TT, et al. 2019; Singh P and Hu LL, et al. 2019) |
| formaldehyde ($CH_2O$) | zinc oxide (ZnO) (Sun J and Sun L, et al. 2019; Jali MH and Rahim HRA, et al. 2019), or tin oxide ($SnO_2$) (Khamfoo K and Inyawilert K, et al. 2020; Li G and Cheng Z, et al. 2019) |
| benzene ($C_6H_6$) | tin oxide ($SnO_2$) (Guo W and Zhou Q, et al. 2019), or carbon nanotube (Grinenval E and James F et al., 2019) |

As such, according to some embodiments, the target molecule to be detected is hydrogen ($H_2$), and the one or more reacting compositions in the composite film layer for the $H_2$ sensing apparatus can comprise at least one of palladium (Pd), metallic La—$Mg_2$—Ni, tungsten trioxide ($WO_3$), carbon nanotubes (CNT), Si nanowires tin dioxide ($SnO_2$), a metal-polymer hybrid nanomaterial, a semiconductor oxide nanostructure, or a core/shell plasmonic nanorod metamaterial.

According to some other embodiments, the target molecule to be detected is ammonia ($NH_3$), and in the ammonia sensing apparatus, the one or more reacting compositions in the composite film layer can comprise at least one of tin oxide ($SnO_2$), zinc oxide (ZnO), tungsten oxide ($WO_3$), titanium oxide ($TiO_2$), iron oxide ($Fe_2O_3/Fe_3O_4$), polyaniline, polypyrrole, metal phthalocyanines, or graphite oxide.

According to some other embodiments, the target molecule to be detected is hydrogen sulfide ($H_2S$), and tungsten oxide ($WO_3$) can be selected as one reacting composition in the composite film layer for the hydrogen sulfide sensing apparatus.

According to yet some other embodiments, the target molecule to be detected is methane ($CH_4$), and tin oxide ($SnO_2$) can be selected as one reacting composition in the composite film layer for the methane sensing apparatus.

According to yet some other embodiments, the target molecule to be detected is nitrogen dioxide ($NO_2$), and copper (II) oxide (CuO) can be selected as one reacting composition in the composite film layer for the nitrogen dioxide sensing apparatus.

According to yet some other embodiments, the target molecule to be detected is carbon monoxide (CO), and titanium oxide ($TiO_2$) can be selected as one reacting composition in the composite film layer for the carbon monoxide sensing apparatus.

According to yet some other embodiments, the target molecule to be detected is nitric oxide (NO), and zinc oxide (ZnO) can be selected as one reacting composition in the composite film layer for the nitric oxide sensing apparatus.

According to yet some other embodiments, the target molecule to be detected is formaldehyde ($CH_2O$), and zinc oxide (ZnO), tin oxide ($SnO_2$), or their combination thereof, can be selected as the reacting composition(s) in the composite film layer for the formaldehyde sensing apparatus.

According to yet some other embodiments, the target molecule to be detected is benzene ($C_6H_6$), and carbon nanotubes, $SnO_2$, or their combination thereof, can be selected as the reacting composition(s) in the composite film layer for the benzene sensing apparatus.

Herein in the composite film layer, the at least two compositions, which include one or more SPR-active compositions and one or more target molecule-reacting compositions, are substantially in a mixed form. In other words, the active composition(s) and the reacting composition(s) are mixed with one another in the composite film layer to thereby confer an improved target-sensing performance such as a faster response time, a faster recovery time, and/or better resistance to deactivation/poisoning, to the sensing apparatus. To obtain the composite film layer, the at least two compositions can be simultaneously formed, coated, or deposited over the outer surface of the optical fiber, which can be realized by means of sputtering, electroplating, or chemical deposition, etc.

Optionally, in the sensing apparatus, the coating assembly further comprises a transition layer, which is sandwiched between the outer surface of the optical fiber and an inner surface of the composite film layer and is configured to improve adhesion of the composite film layer to the optical fiber. According to different embodiments, the transition layer can have a composition of titanium (Ti), molybdenum (Mo), chromium (Cr), or any of their combinations. For example, the transition layer can be a film layer of chromium (Cr) having a thickness of approximately 2-3 nm, or can be a film layer of titanium (Ti) having a thickness of approximately 3-5 nm. Other compositions can also be chosen for the transition layer.

Further optionally, the coating assembly can further include an SPR-active substrate layer that is immediately below the composite film layer so as to enhance the SPR signal detection. The substrate layer can comprise one or more SPR-active compositions as described above.

Further optionally, a transition layer, a substrate layer, and a composite film layer can be sequentially formed over an outer surface of the optical fiber to thereby form the coating assembly.

In the sensing apparatus, the composite film layer can have a thickness in range of approximately 25-75 nm, and for example, can have a thickness between 40-60 nm.

In the sensing apparatus, an internal tilt angle of the tilted grating can be at least approximately 20 degrees, and for example, can be around 23 degrees.

More specifically in the embodiments of the hydrogen ($H_2$) sensing apparatus where palladium (Pd) represents one of the one or more reacting compositions in the composite film layer, optionally a weight concentration of palladium (Pd) in the composite film layer can be in a range of approximately 20%-80%, and for example, of approximately 40-50%. Further optionally, the composite film layer can have a thickness in range of approximately 25-75 nm, and for example, of approximately 40-60 nm. Further optionally, gold (Au) is selected as the active composition in the composite film layer of the coating assembly, and in these embodiments, the reacting composition palladium (Pd) and the active composition gold (Au) substantially form an alloy in the composite film layer. Further optionally in the coating assembly, a film layer of chromium having a thickness of approximately 2-3 nm can be used as the transition layer between the outer surface of the optical fiber and the inner surface of the composite film layer (i.e. the Pd—Au alloy film layer) so as to improve the adhesion of the composite film layer onto the optical fiber. Further optionally, an internal tilt angle of the tilted grating can be at least approximately 20°, for example, approximately 23°.

Due to the presence of the composite film layer in the coating assembly which has the SPR-active composition and the target molecule-reacting composition in a mixed form, the sensing apparatus disclosed herein not only allows for a sensitive detection of target molecules in the gas medium, but also has additional advantages including relatively faster response and limited deactivation caused by poisoning, if compared with the sensing apparatus without such a configuration.

In the following, with reference to the drawings, a more detailed description is provided for the various embodiments of the sensing apparatus and system, of a method of manufacturing the sensing apparatus, as well as of a method of use thereof.

Figure 1B:
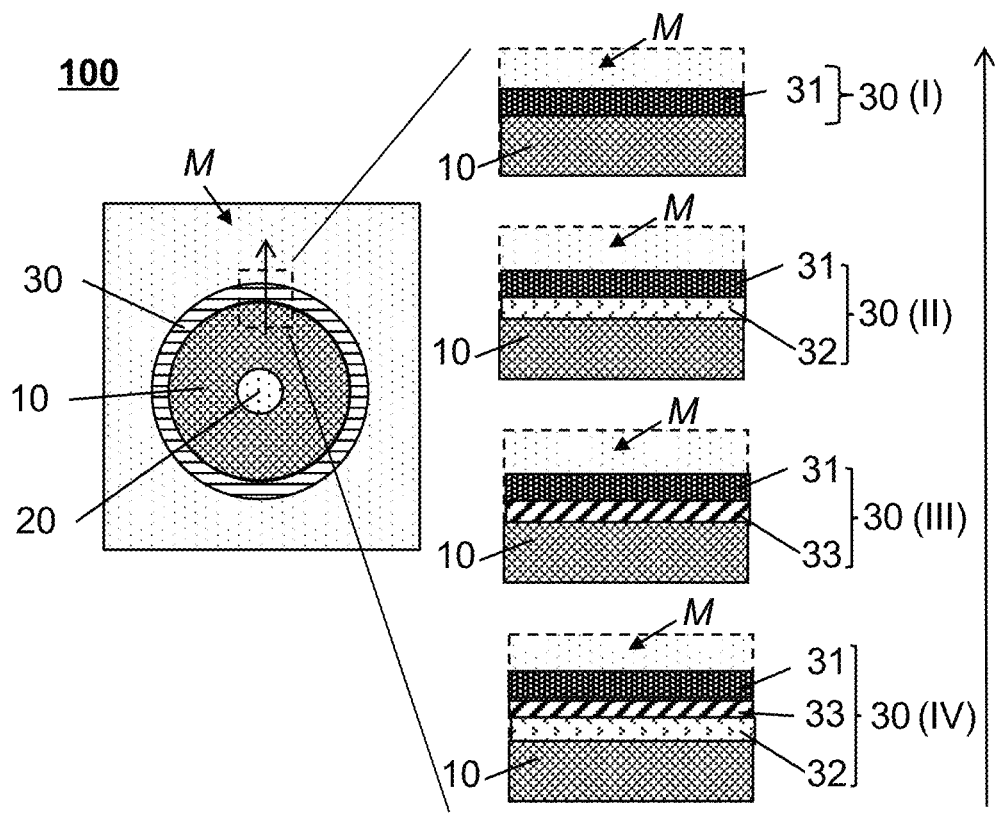

FIGS. 1A and 1B respectively illustrate a perspective view and a cross-sectional view of a sensing apparatus according to some embodiments of the disclosure.

FIG. 1A illustrates a perspective view, and a working mechanism of the sensing apparatus. As illustrated, the sensing apparatus 100 includes a core 20 and a cladding 10, which are arranged coaxially to together form an optical fiber. A coating assembly 30 coats the cladding 10 of the optical fiber, with its outer surface exposing to, or in direct contact with, the medium M.

The core 20 of the optical fiber is provided with a tilted grating 12, i.e. a grating having an internal tilt angle θ (defined as an angle of each plane of the grating relative to a plane that is substantially perpendicular to the axis of the core 20) of more than 0°. Upon an input light 1 entering from a first side surface A into the optical fiber and transmitting substantially along the core 20, the tilted grating 12 can reflect and/or refract the input light into the cladding 10 of the optical fiber (the light such reflected or refracted is shown as 2 in FIG. 1A), exciting plasmon waves 3 in the cladding and surface plasmon waves 4 at an interface between the coating assembly 30 and the medium M.

In addition, the sensing apparatus 100 can also generate optical waves in the core 20 of the optical fiber (i.e. core-mode optical waves, not shown in the above drawings) which, if detected, can be used as an inherent reference when doing the analysis of the surface plasmon waves 4 to thereby remove the unwanted influence, or interference, due to fluctuations from certain factors, such as those from the environment (e.g. temperature) or those from the sensing system (e.g. light source level). As such, the sensing apparatus 100 disclosed herein can have a feature of be capable of self-calibration.

The sensing apparatus 100 also has a second side surface B opposing to the first side surface A, and could be the light emitting surface (e.g. for a transmission-mode optical fiber), or could be a light reflecting surface (e.g. for a reflection-mode optical fiber). In the latter case, a mirror can be arranged on the second side surface, and will be described below in more detail.

The cross-sectional view of the sensing apparatus 100 as shown in FIG. 1A is further illustrated in FIG. 1B. As illustrated, in the optical fiber, the core 20 and the cladding 10 are arranged coaxially, and the coating assembly 30 coats an outer surface of the cladding 10 of the optical fiber, and has its outer surface in direct contact with the medium M.

As further illustrated in FIG. 1B, the coating assembly 30 can have different configurations according to different embodiments. According to a first configuration (I), the coating assembly 30 substantially includes one single film layer (i.e. composite film layer 31), which both coats the cladding 10 of the optical fiber and is exposed to the medium M. The composite film layer 31 is configured to contain two or more compositions which are mixed with one another to thereby form a mixture. At least one of the compositions contained in the composite film layer 31 is configured to be active to surface plasmon resonance (SPR), and at least one of the compositions contained in the composite film layer 31 is further configured to be reversibly reactive to the target molecule so as to cause a change of the SPR allowing for the deduction of characteristics of the target molecule in the medium M. Together the co-presence of the SPR-active composition(s) and the target molecule-reactive composition(s) in the composite film layer 31 allows it to be both active to SPR and sensitive or reactive to the target molecule in the medium M.

Optionally, according to a second configuration (II) illustrated also in FIG. 1B, the coating assembly 30 further includes a transition layer 32, which is sandwiched between the outer surface of the cladding 10 (i.e. the upper surface thereof in the figure) of the optical fiber and an inner surface (i.e. the lower surface thereof in the figure) of the composite film layer 31. The transition layer 32 is configured to improve adhesion of the composite film layer 31 to the optical fiber.

Further optionally, according to a third configuration (III) illustrated also in FIG. 1B, the coating assembly 30 may further include a substrate layer 33, sandwiched between an outer surface of the cladding 10 (i.e. the upper surface shown in the figure) of the optical fiber and an inner surface of the composite film layer 31 (i.e. the lower surface thereof in the figure). The substrate layer 33 is configured to be active to SPR and insensitive to the target molecules in the medium M.

Further optionally, according to a fourth configuration (IV) illustrated also in FIG. 1B, the coating assembly 30 may include a transition layer 32, a substrate layer 33, and the composite film layer 31, which are sequentially arranged over one another over the outer surface of the cladding 10 (i.e. the upper surface thereof in the figure) of the optical fiber.

In any of the embodiments described above, the compositions, thicknesses, and other relevant features for the transition layer 32, the substrate layer 33, and the composite film layer 31 can be referenced to the description above and are not detailed herein.

The input light 1 as referred to above and illustrated in FIGS. 1A and 1B shall be understood as a suitable electromagnetic radiation emitted by a light source apparatus that can, upon reflection and refraction by the tilted grating, excite or induce the generation of surface plasmon waves 4 at an interface between the coating assembly 30 and the medium M to allow the analysis of the change of refracting indices in the medium M to derive information of the target molecules in the medium M Preferably the input light 1 can be a polarized light having a polarization direction substantially parallel to an inscription direction (e.g. each plane of the grating 12) of the tilted grating 12 in the core 20 of the optical fiber. Yet a non-polarized light, or a polarized light with a polarization direction other than that perpendicular to the inscription direction of the tilted grating 12 can also be used as the input light 1 to thereby excite the generation of the surface plasmon waves 4.

Furthermore, in any of the embodiments of the sensing apparatus described above, the optical fiber can have components, compositions, dimensions, and/or configurations of the optical fibers mentioned in any of the embodiments that follow, such as those use for telecommunications-grade optical fiber (e.g. Corning SMF-28), but can also have other parameters.

In a second aspect, a sensing system comprising any of the embodiments of the sensing apparatus as described and illustrated above in the first aspect is further provided.

In addition to the sensing apparatus, the sensing system further includes a light source apparatus and a signal detection apparatus, which are both optically and communicatively coupled with the sensing apparatus, and are configured respectively to provide an input light into the sensing apparatus, and to obtain signals of the surface plasmon waves induced at the medium-coating assembly interface from the sensing apparatus, so as to derive the information of the target molecule in the medium to realize the detection of the target molecule.

More specifically, the light source apparatus is optically coupled to a first end of, and configured to provide an input light into, the sensing apparatus so as to allow the electromagnetic radiation to propagate in the core of the optical fiber of the sensing apparatus; and the signal detection apparatus is coupled to the sensing apparatus and configured to obtain the signals of the surface plasmon waves therefrom so as to derive the information of the target molecule in the gaseous medium.

Depending on the different working mode, the sensing system has at least three configurations: a transmission mode and a reflection mode.

Figure 2A:
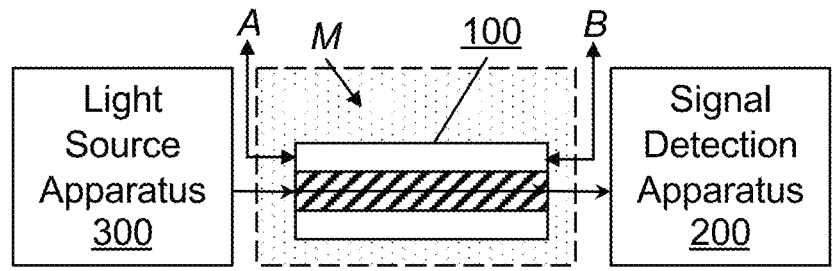
FIG. 2A is a block diagram of a transmission-mode sensing system according to some embodiments of the disclosure.

FIG. 2A is a block diagram of a transmission-mode sensing system according to some embodiments of the disclosure. As shown, the sensing system 1000 includes one sensing apparatus 100, optically and communicatively arranged between a light source apparatus 300 and a signal detection apparatus 200 along a direction of light transmission (as shown by the rightward arrows in the figure). In other words, the light source apparatus 300 is optically coupled to a light-incident surface A of the sensing apparatus 100 and thus sends an input light through the light-incident surface A into the optical fiber (as shown by the block with a pattern of inclining lines in FIG. 2A) of the sensing apparatus 100, whereas the signal detection apparatus 200 is optically coupled to a light-emitting surface B of the sensing apparatus 100, and thus receives optical signals (i.e. signal of the SPR waves and core-mode optical waves) transmitted through the light-emitting surface B from the sensing apparatus 100.

It is noted that the transmission-mode configuration as above allows for multiplexing of more than one sensing apparatus in one single sensing system, in which the optical fibers of the more than one sensing apparatus share a common light transmission pathway between one single light source apparatus and one single signal detection apparatus. It is further noted in the transmission-mode sensing system described herein, any of the sensing apparatuses such multiplexed with each other can be based on any of the embodiments of the sensing apparatus as described above in the first aspect, or can be based on any of the embodiments of the sensing apparatus as described in the U.S. patent application Ser. No. 16/382,186.

Figure 2B:
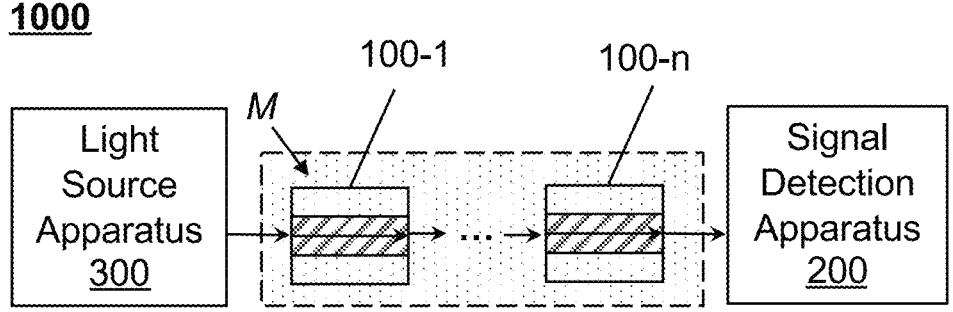
FIGS. 2B-2E are respectively a block diagram of a transmission-mode sensing system having multiplexed sensing apparatuses according to several different embodiments of the disclosure.

According to one embodiment illustrated in FIG. 2B, each of the more than one sensing apparatus (100-1, 100-2, . . . , 100-*n*) such multiplexed can be configured to have a different reactivity to a different target molecule (T1, T2, . . . , and Tn, which are not shown in the figure) in a common medium M so as to realize simultaneous detection of a variety of different target molecules (T1, T2, . . . , Tn) in the medium M using one single sensing system 1000.

Figure 2C:
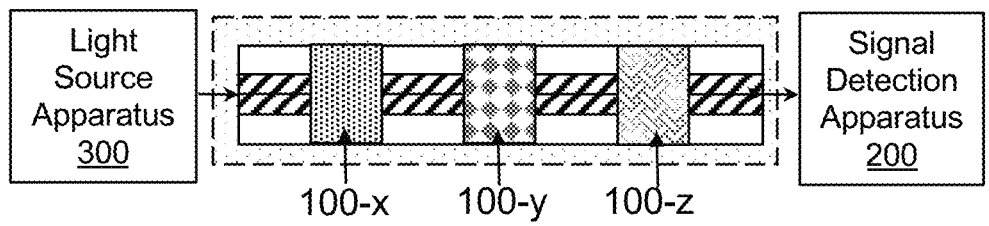

Further optionally, more than one sensing apparatus (100-1, 100-2, . . . , 100-*n*) can share one single optical fiber, yet are configured to have a different coating assembly arranged at a different region on the outside surface of the cladding of the optical fiber along a direction of light transmission in the core, as illustrated in FIG. 2C which shows three sensing apparatuses (100-*x*, 100-*y*, and 100-*z*) arranged on a single optical fiber.

It is noted that optionally, the more than one sensing apparatus (100-1, 100-2, . . . , 100-*n*) do not share one single optical fiber, yet are optically connected in series through other optical connecting means (such as an optical connector). There are no limitations herein.

Figure 2D:
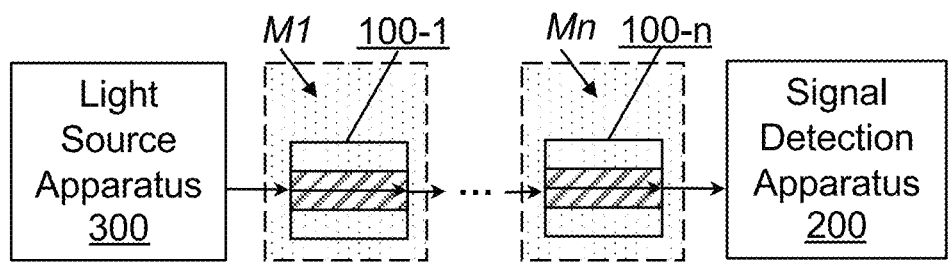

According to some other embodiments illustrated in FIG. 2D, each of the more than one sensing apparatus (100-1, 100-2, . . . , 100-*n*) such multiplexed can be configured to have a different reactivity to a different target molecule (T1, T2, . . . , Tn), each arranged in a different medium (M1, M2, . . . , Mn) and connected to a commonly shared light source apparatus 300 and a commonly shared signal detection apparatus 200, as such simultaneous detection of different target molecules (T1, T2, . . . , Tn) in different medium (M1, M2, . . . , Mn) can be realized.

Figure 2E:
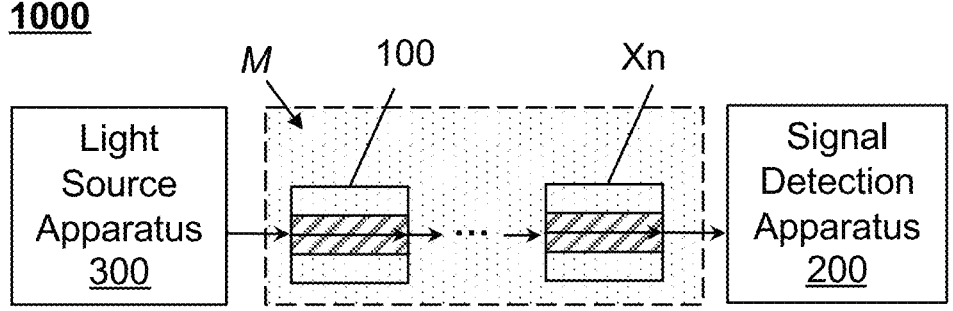

It is noted that in addition to the above embodiments where the more than one sensing apparatus are each configured to detect a target molecule, at least one (Xn) of these multiplexed sensing apparatuses may be configured for detection of a physical property, such as a temperature, a humidity, a pressure, etc., of a medium Min which the sensing apparatus Xn is disposed. As such, simultaneous detection of a variety of physical and chemical characteristics of the medium by means of one single sensing system 1000 as shown in FIG. 2E having one shared light source apparatus 300 and one shared signal detection apparatus 200 can be realized.

Figure 3A:
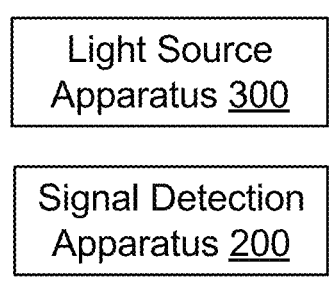
FIG. 3A is a block diagram of a reflection-mode sensing system according to some embodiments of the disclosure.

FIG. 3A is a block diagram of a reflection-mode sensing system according to some embodiments of the disclosure. As shown, the light source apparatus 300 and the signal detection apparatus 200 are substantially arranged over a same side of the sensing apparatus 100. Specifically, the light source apparatus 300 and the signal detection apparatus 200 are both optically coupled to a first end A of the optical fiber of the sensing apparatus 100, whereas a second end B is provided with a mirror 101, which has a reflection surface facing to, configured to reflect the light back towards, the first end A of the optical fiber. As such, the first end A is substantially a light-incident surface of the optical fiber, through which the input light provided by the light source apparatus 300 can enter into the optical fiber of the sensing apparatus 100. Then after reflection at the second end B of the optical fiber by the mirror 101, reflected light can transmit back through the first end A to be received by the signal detection apparatus 200.

In order to separate an input optical pathway and an output optical pathway to thereby allow the signal detection apparatus to obtain the signals of the surface plasmon waves from the sensing apparatus without being influenced by the input light, the sensing system 1000 further comprises a coupler 400, which is arranged between the light source apparatus 300 and the sensing apparatus 100 along the input optical pathway and between the sensing apparatus 100 and the signal detection apparatus 200 along the output optical pathway.

Figure 3B:
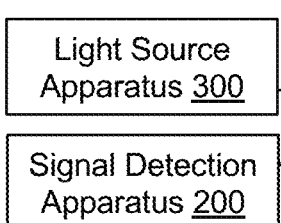
FIG. 3B is a block diagram of a reflection-mode sensing system having multiplexed sensing apparatuses according to some embodiments of the disclosure.

Similar to the transmission-mode sensing system, as illustrated in FIG. 3B, the reflection-mode sensing system can also realize multiplexing of more than one sensing apparatuses, wherein the more than one sensing apparatus 100 can be optically coupled one another in series and connected to the coupler 400.

In any one embodiment of the sensing system 100 described above, the light source apparatus 300 can include a light source, a polarizer, and a polarization controller (PC). Herein the light source can be a broadband source (BBS) or a tunable laser source (TLS). Light emitted from the light source can be converted into a polarized light having a polarization direction substantially parallel to an inscription direction of the tilted grating after the emitted light transmits through the polarizer and the polarization controller.

Figure 4A:
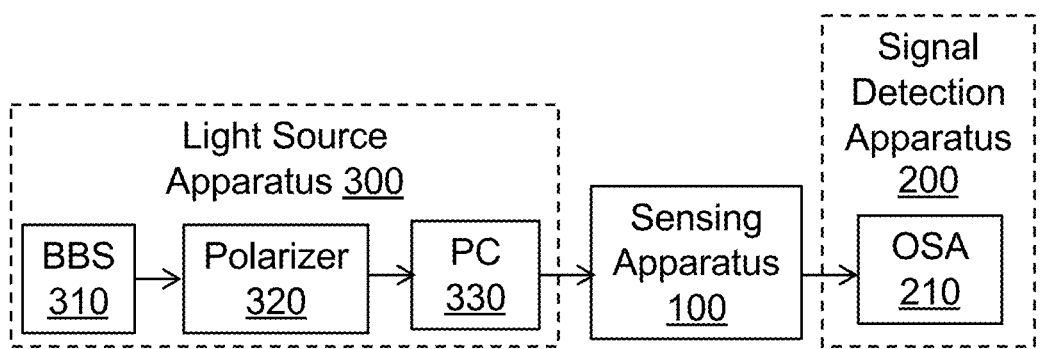
FIGS. 4A and 4B respectively shows a block diagram of a sensing system according to two different embodiments of the disclosure.

According to some embodiments of the sensing system 1000 as illustrated in FIG. 4A, the light source apparatus 300 can include a broadband source (BBS) 310, a polarizer 320, and a polarization controller (PC) 330, and in accordance, the signal detection apparatus 200 comprises an optical spectrum analyzer (OSA) 210. The broadband source (BBS) 310 can provide a broadband input light, which can be converted, via the polarizer 320 and the polarization controller (PC) 330, into a polarized light with aforementioned polarization direction before it enters into the optical fiber of the sensing apparatus so as to excite surface plasmon waves on the surface of the sensing apparatus 100. The optical spectrum analyzer (OSA) 210 is configured to analyze, via a spectral interrogation, the signals of the surface plasmon waves transmitted from the sensing apparatus 100 to quantify a wavelength shift and optical intensity change induced by a refractive index change of the sensing apparatus 100 so as to in turn derive information of, or characterize, the target molecule in the medium.

Figure 4B:
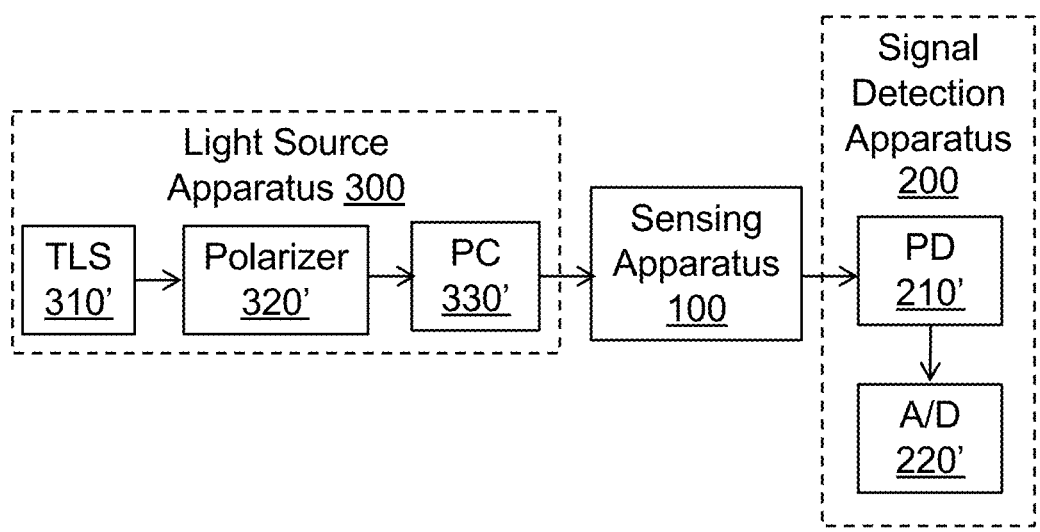

According to some other embodiments of the sensing system 1000 as illustrated in FIG. 4B, the light source apparatus 300 can include a tunable laser source (TLS) 310', a polarizer 320', and a polarization controller (PC) 330', and in accordance, the signal detection apparatus 200 comprises an optical detector (PD) 210' and an analog-to-digital converter (A/D) 220'. The tunable laser source (TLS) 310' is configured to provide an input light with a predetermined narrow band, such as comprising a light with a second wavelength matching a predetermined first wavelength. A light with the predetermined first wavelength has been determined in advance to be able to produce one of the most sensitive modes of surface plasmon waves on the sensing apparatus, upon being inputted into the sensing apparatus. The pre-determination can be performed utilizing the embodiments of the sensing system as illustrated in FIG. 4A, where the sensing apparatus 100 to be examined is coupled to a broadband source (BBS) 310, a polarizer 320, a polarization controller (PC) 330, and an optical spectrum analyzer (OSA) 210 in a configuration illustrated in FIG. 4A. The broadband source (BBS) 310 is configured to provide a broadband input light, whereas an optical spectrum analyzer (OSA) 210 is configured to analyze at which wavelength the input light can generate one of the most sensitive modes of surface plasmon waves on the sensing apparatus 100.

The input light is further converted, via the polarizer 320' and the polarization controller (PC) 330', into a polarized light with aforementioned polarization direction before it enters into the optical fiber of the sensing apparatus so as to excite surface plasmon waves on the surface of the sensing apparatus 100. The optical detector 210' is configured to detect, and to convert into analog electrical signals, the signals of the plasmon waves from the sensing apparatus 100. The analog-to-digital converter 220' is further configured to convert the analog electrical signals into digital electrical signals, based on which an interrogation can be performed over a quantification of intensity variations to thereby derive the information of the target molecule in the medium.

In a third aspect of the disclosure, a method for selectively detecting a target molecule in a medium utilizing the aforementioned sensing system is further provided.

Figure 5A:
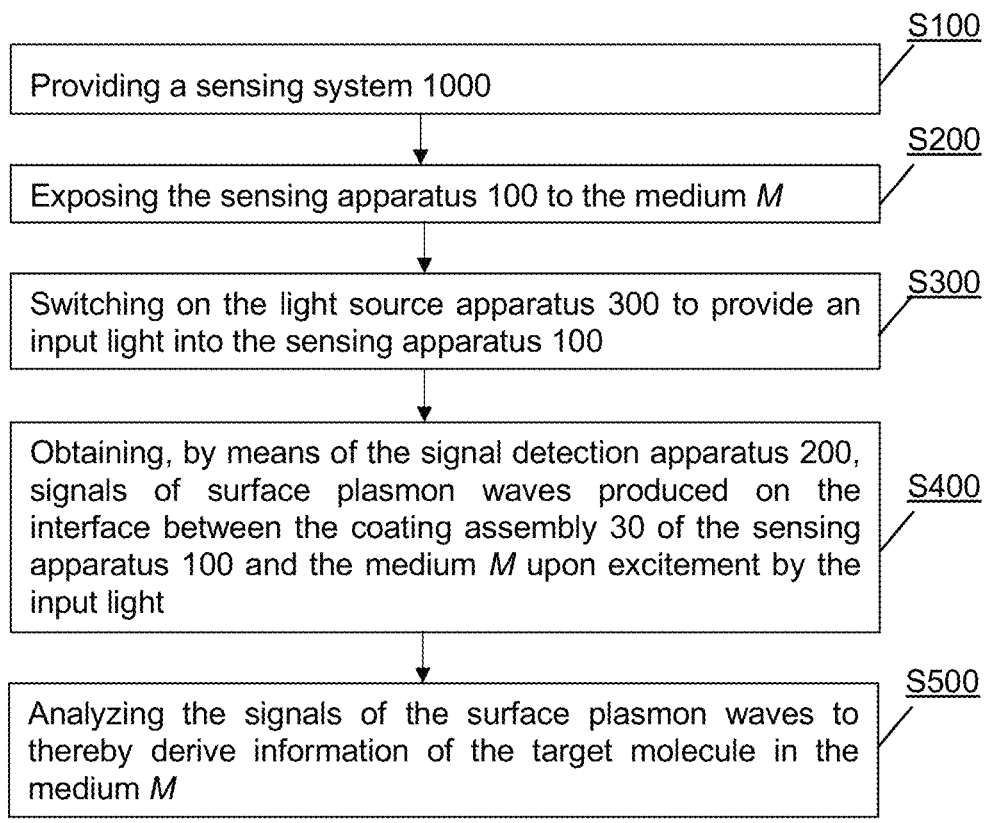
FIGS. 5A-5E respectively illustrate a flow chart of a method of using the sensing system according to different embodiments of the disclosure.

FIG. 5A illustrates a flow chart of the method according to some embodiments of the disclosure. As shown, the method comprises the following steps:

S100: Providing a sensing system 1000;

S200: Exposing the sensing apparatus 100 to the medium M;

S300: Switching on the light source apparatus 300 to provide an input light into the sensing apparatus 100;

S400: Obtaining, by means of the signal detection apparatus 200, signals of surface plasmon waves produced on the interface between the coating assembly 30 of the sensing apparatus 100 and the medium M upon excitement by the input light; and S500: Analyzing the signals of the surface plasmon waves to thereby derive the information of the target molecule in the medium M.

Figure 5B:
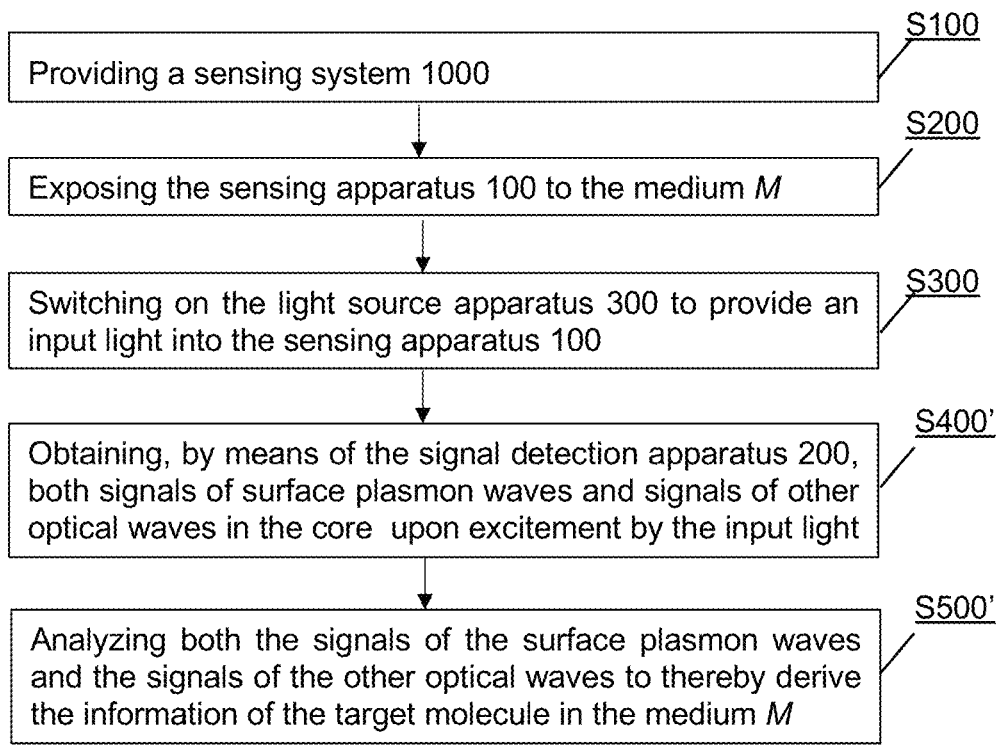

According to some embodiments of the sensing system 1000, the sensing apparatus 100 is configured to be able to generate optical waves in the core 20 of the optical fiber which, if detected, can be used as an inherent reference when doing the analysis of the surface plasmon waves 4 to thereby remove the unwanted influence, or interference, due to fluctuations from certain factors, such as those from the environment (e.g. temperature) or those from the sensing system (e.g. light source level). As such, according to some embodiments of the method illustrated in FIG. 5B, rather than only obtaining signals of signals of surface plasmon waves, step S400 comprises:

S400': Obtaining, by means of the signal detection apparatus 200, both signals of the surface plasmon waves and signals of other optical waves in the core. Accordingly, step S500 comprises:

S500': Analyzing both the signals of the surface plasmon waves and the signals of the other optical waves to thereby derive the information of the target molecule in the medium M.

Figure 5C:
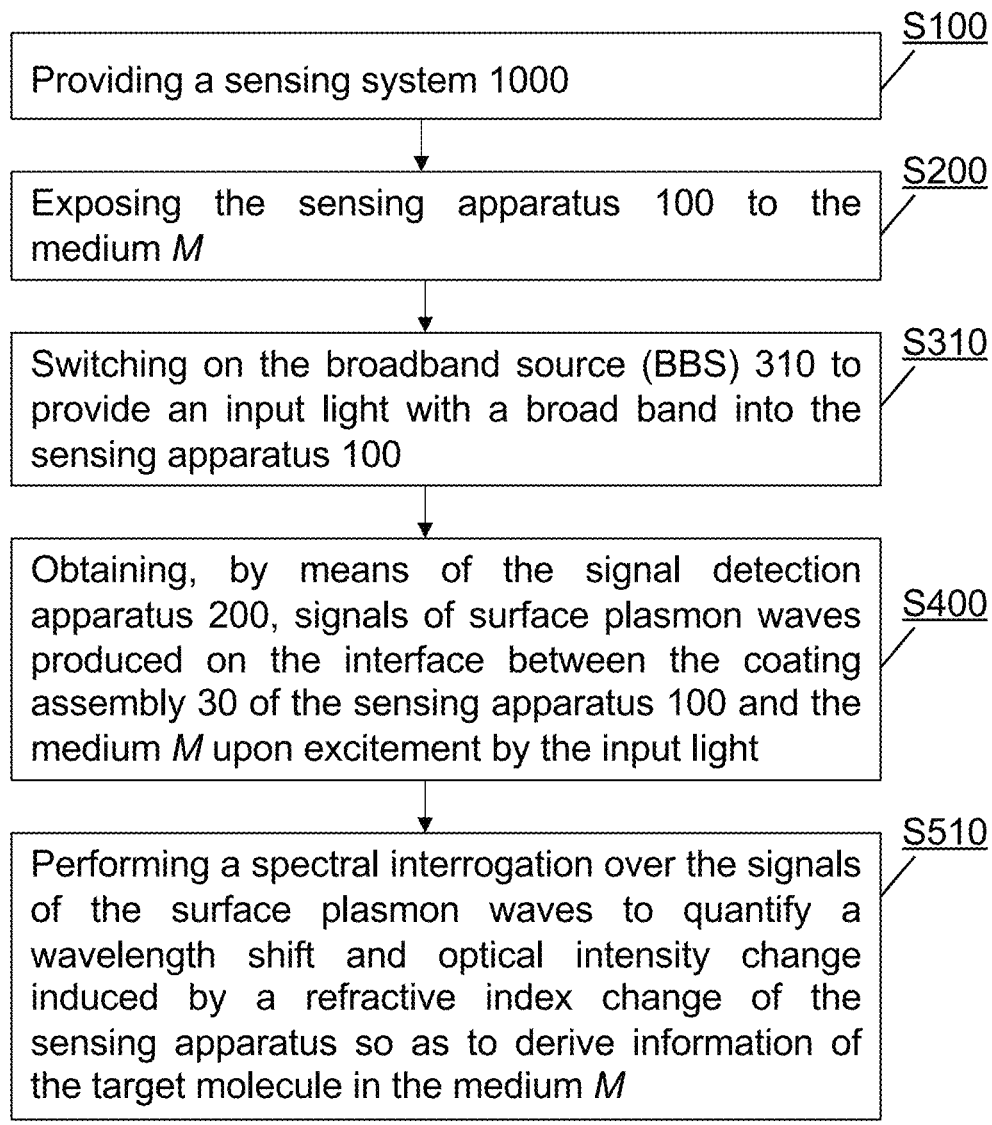

According to some embodiments, the light source apparatus 300 of the sensing system 1000 comprises a broadband source (BBS) 310, and the signal detection apparatus 200 comprises an optical spectrum analyzer (OSA) 210, as illustrated in FIG. 4A. As such, in the embodiments of the method utilizing the sensing system 100 as above, which is illustrated in FIG. 5C, step S300 of switching on the light source apparatus 300 to provide an input light into the sensing apparatus 100 comprises:

S310: Switching on the broadband source (BBS) 310 to provide an input light with a broad band into the sensing apparatus 100.

Further correspondingly, step S500 of analyzing the signals of the surface plasmon waves comprises:

S510: Performing a spectral interrogation over the signals of the surface plasmon waves to quantify a wavelength shift and optical intensity change induced by a refractive index change of the sensing apparatus so as to derive information of the target molecule in the medium M.

Figure 5D:
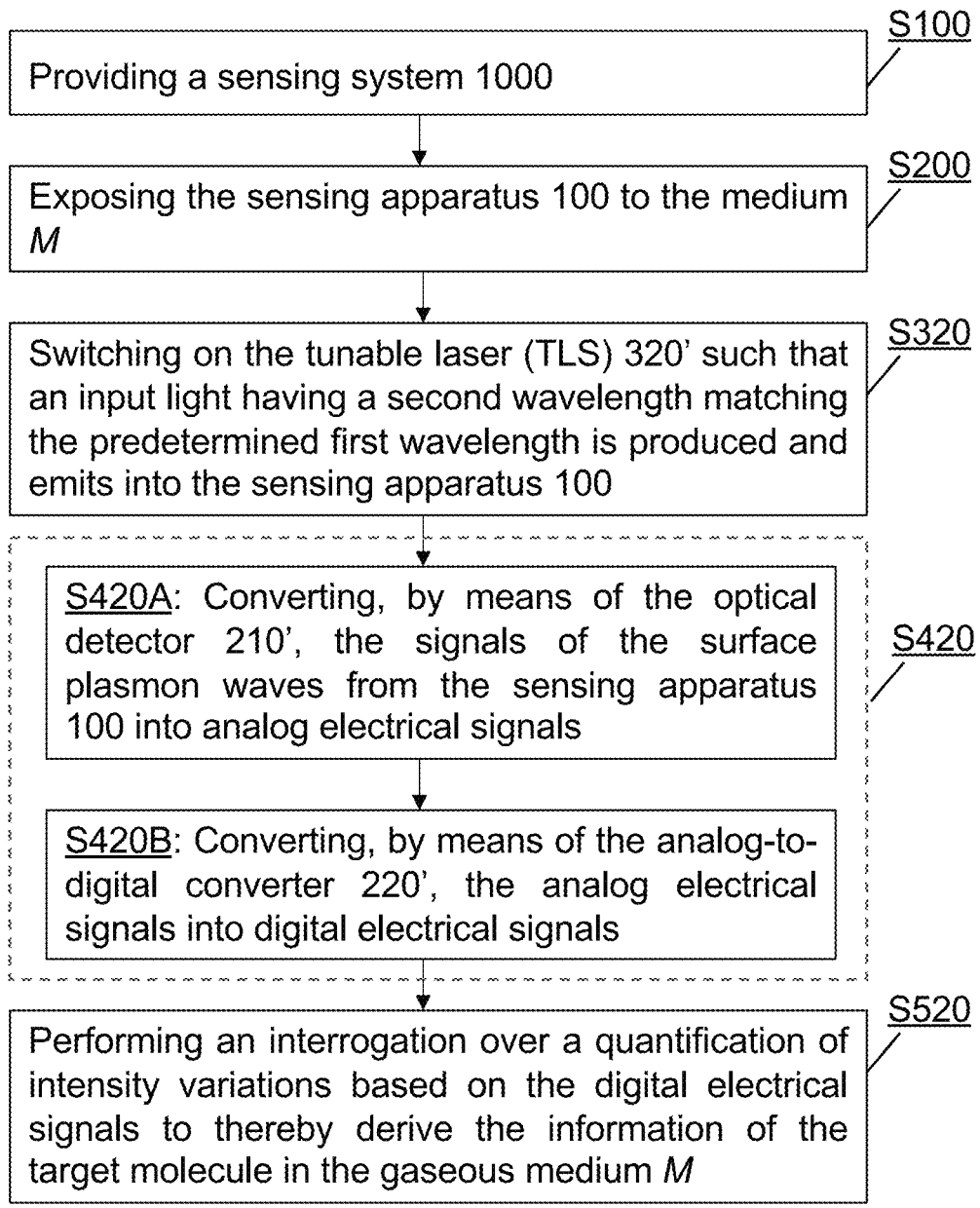

According to some other embodiments, the light source apparatus 300 of the sensing system 1000 comprises a tunable laser source (TLS) 310', and the signal detection apparatus 200 comprises an optical detector (PD) 210' and an analog-to-digital converter (A/D) 220', as illustrated in FIG. 4B. As such, in some embodiments of the method utilizing the sensing system as above, which is illustrated in FIG. 5D, step S300 of switching on the light source apparatus 300 to provide an input light into the sensing apparatus 100 comprises:

S320: Switching on the tunable laser (TLS) such that an input light having a second wavelength matching the predetermined first wavelength is produced and emits into the sensing apparatus 100.

Correspondingly, step S400 of obtaining, by means of the signal detection apparatus 200, signals of surface plasmon waves produced on the interface between the coating assembly 30 of the sensing apparatus 100 and the medium M upon excitement by the input light comprises:

S420A: Converting, by means of the optical detector 210', the signals of the surface plasmon waves from the sensing apparatus 100 into analog electrical signals; and S420B: Converting, by means of the analog-to-digital converter 220', the analog electrical signals into digital electrical signals.

Further correspondingly, step S500 of analyzing the signals of the surface plasmon waves to thereby derive the information of the target molecule in the gaseous medium M comprises:

S520: Performing an interrogation over a quantification of intensity variations based on the digital electrical signals to thereby derive the information of the target molecule in the gaseous medium M.

Figure 5E:
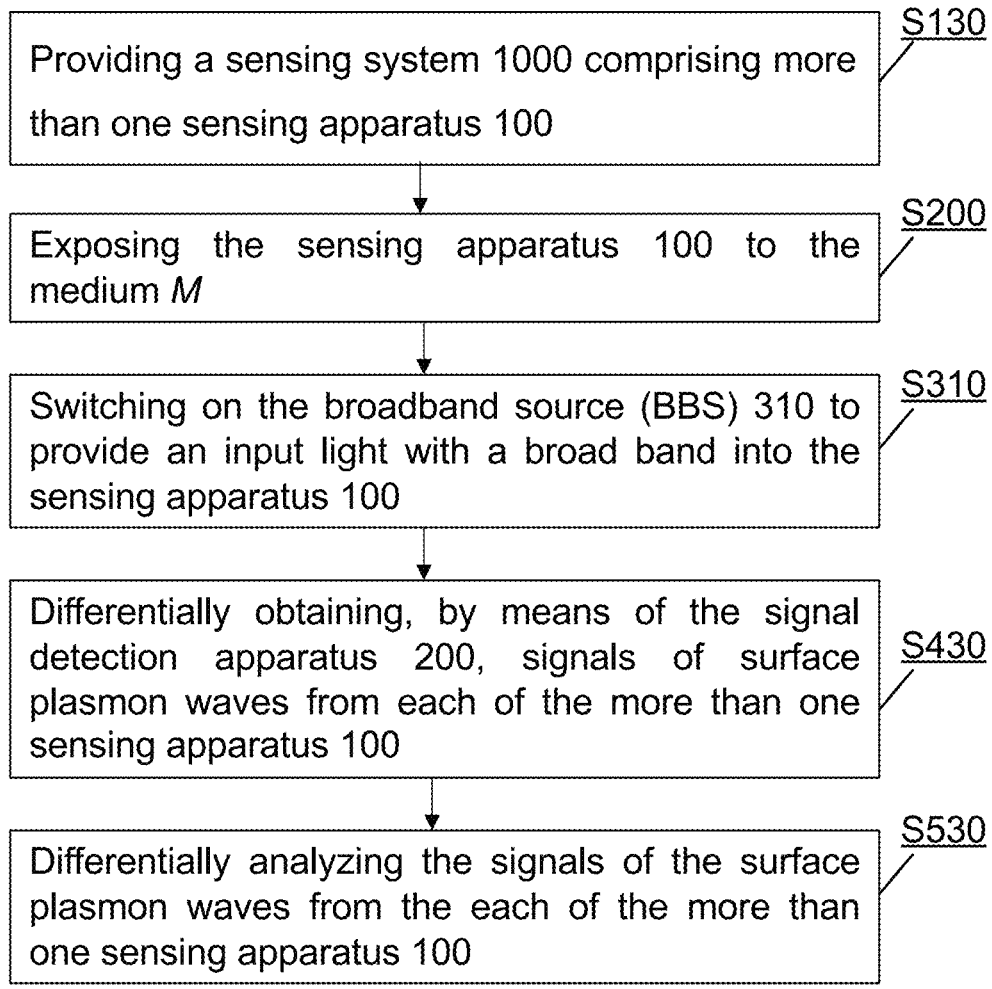

According to some embodiments, the sensing system 1000 comprises more than one sensing apparatus, which are multiplexed (i.e. optically connected to one another in series and each comprising an optical fiber sharing a common electromagnetic radiation propagation pathway), as illustrated in FIG. 2D or FIG. 3B. As such, in embodiments of the method utilizing the sensing system 1000 as above, which is illustrated in FIG. 5E, the step S100 comprises:

S130: Providing a sensing system 1000 comprising more than one sensing apparatus 100;

Correspondingly, the step S400 of obtaining, by means of the signal detection apparatus, signals of surface plasmon waves produced on the interface between the coating assembly and the gaseous medium upon excitement by the input light comprises:

S430: Differentially obtaining, by means of the signal detection apparatus 200, signals of surface plasmon waves from each of the more than one sensing apparatus 100.

Further correspondingly, the step S500 of analyzing the signals of the surface plasmon waves comprises:

S530: Differentially analyzing the signals of the surface plasmon waves from the each of the more than one sensing apparatus 100.

In a fourth aspect, a method for manufacturing the sensing apparatus as described in the first aspect of the disclosure is also provided.

Figure 6A:
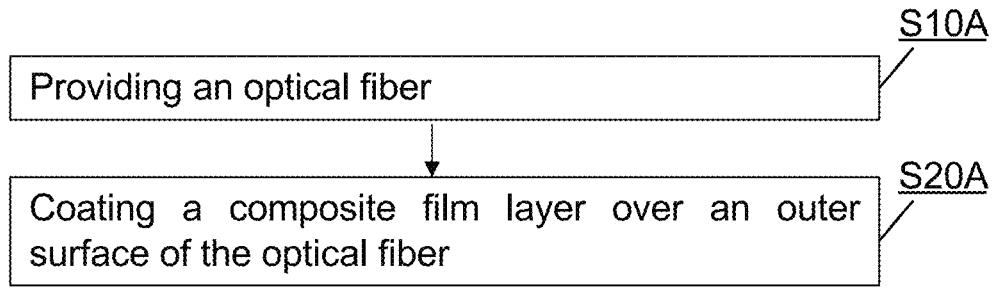
FIGS. 6A-6D respectively show the flow charts of four different embodiments of a manufacturing method of a sensing apparatus having the four configurations illustrated in FIG. 1B.

As illustrated in FIG. 6A, some embodiment of the manufacturing method comprises the following steps:

S10A: providing an optical fiber;

Herein in this step, the optical fiber that is provided comprises a core and a cladding surrounding the core, and the core is provided with a tilted grating, which is configured to generate surface plasmon waves at an interface between the coating assembly and the gaseous medium upon a compatible electromagnetic radiation propagating in the optical fiber.

S20A: coating a composite film layer over an outer surface of the optical fiber.

Herein in this step, the composite film layer comprises at least two compositions mixed with one another therein, which contain one or more active compositions and one or more reacting compositions. Each active composition is configured to be active to surface plasmon resonance (SPR), and each reacting composition is configured to be reversibly reactive to the target molecule.

The step S20 of coating a composite film layer over an outer surface of the optical fiber can be realized by means of various coating approaches, including sputtering, electroplating, or chemical deposition.

According to some embodiments of the manufacturing method, the step S20 is realized by means of sputtering. As such, the step S20 comprises:

S21: simultaneously sputtering the at least two compositions to the optical fiber while the optical fiber is rotating about an axis thereof.

In embodiments of the sensing apparatus where each of the at least two compositions in the composite film layer is a metal, and the step S21 can be by means of a single common radio-frequency power source.

By means of the embodiment of the manufacturing method illustrated in FIG. 6A, a sensing apparatus having the first configuration (I) illustrated in FIG. 1B is manufactured, where the coating assembly 30 substantially includes one single composite film layer 31.

Figure 6B:
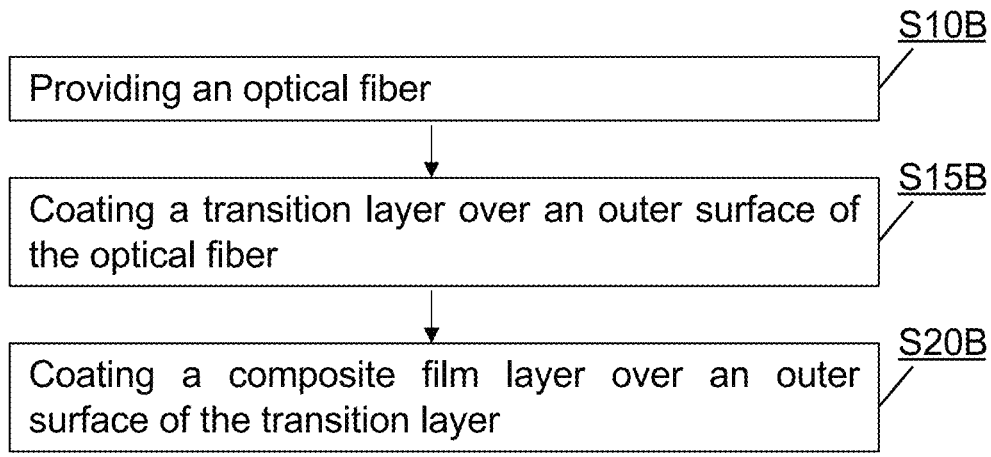

In order to manufacture a sensing apparatus having the second configuration (II) illustrated in FIG. 1B, according to some embodiments illustrated in FIG. 6B, the manufacture method substantially includes the following steps:

S10B: providing an optical fiber;

S15B: coating a transition layer over an outer surface of the optical fiber; and S20B: coating a composite film layer over an outer surface of the transition layer.

Figure 6C:
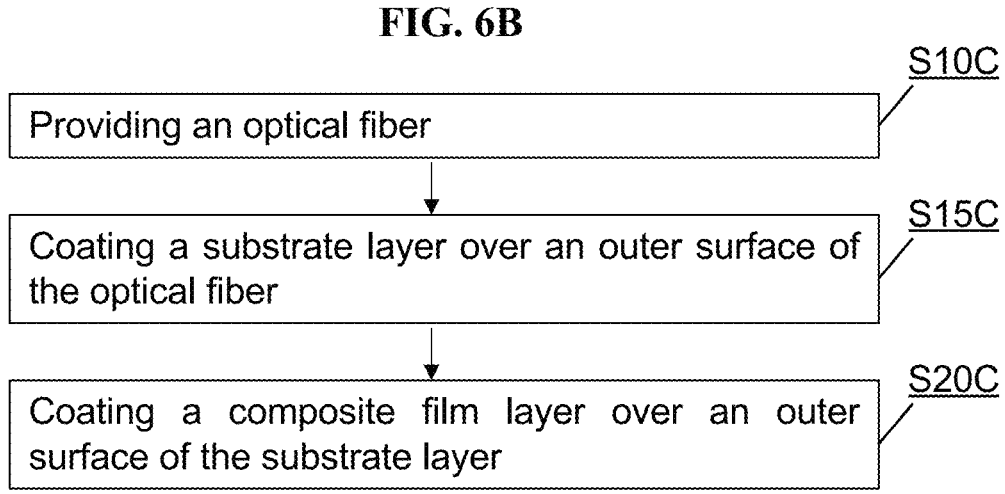

In order to manufacture a sensing apparatus having the third configuration (III) illustrated in FIG. 1B, according to some embodiments illustrated in FIG. 6C, the manufacture method substantially includes the following steps:

S10C: providing an optical fiber;

S15C: coating a substrate layer over an outer surface of the optical fiber; and S20C: coating a composite film layer over an outer surface of the substrate layer.

Figure 6D:
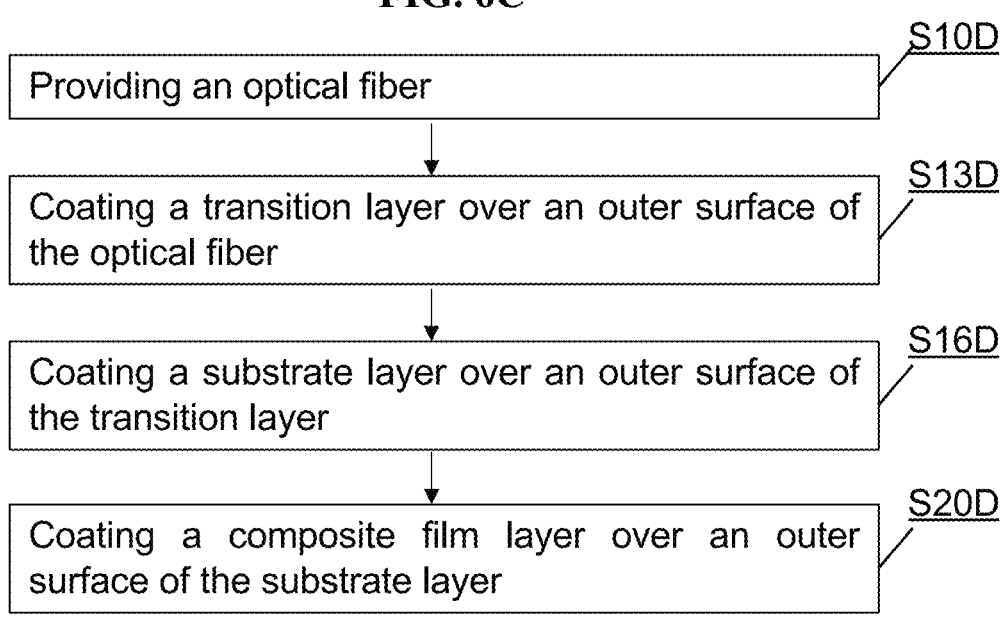

In order to manufacture a sensing apparatus having the fourth configuration (IV) illustrated in FIG. 1B, according to some embodiments illustrated in FIG. 6D, the manufacture method substantially includes the following steps:

S10D: providing an optical fiber;

S13D: coating a transition layer over an outer surface of the optical fiber;

S16D: coating a substrate layer over an outer surface of the transition layer; and S20D: coating a composite film layer over an outer surface of the substrate layer.

In the following, multiple embodiments are provided for a more detailed illustration of the sensing apparatus, system, and the use method for the detection of target molecules in the gas medium.

Embodiment 1

Introduction

Human behavior and an economy founded on fossil fuels have degraded our living environment and climate for centuries. Thus, seeking renewable alternatives to fossil fuel combustion would considerably improve air quality and reduce energy consumption 1. Hydrogen is a high energy-density, carbon-free, renewable and zero-pollution energy carrier. For safety reasons, any leaks in hydrogen energy storage systems, vehicles, and appliances, as well as the entire hydrogen distribution infrastructure, must be detected immediately. In the quest to meet these challenging targets, optical fiber hydrogen sensors based on hydride-forming metal nanoparticles have been studied. These optical sensors are attractive because of their numerous advantages, such as safety, corrosion resistance, and suitability for remote sensing. Furthermore, as opposed to electrical signals, the optical signals generate no sparks. The sensing function stems from the absorption of hydrogen species into interstitial sites of the metal host, which renders such sensors intrinsically highly hydrogen-selective. In this field, palladium (Pd) is one of the most popular and widely used functional materials for specific hydrogen detection. This is because Pd undergoes a reversible phase transition from metal to metal hydride when hydrogen is captured within the Pd crystal lattice at room temperature 16, which consequently modifies the optical properties and effectively modulates the optical and dielectric constants.

However, a widely encountered problem is that some natural gases, like CO and $NO_2$, even at ppm concentrations, can poison the hydrogen dissociation and diffusion into the Pd crystal lattice. This poisoning of the Pd results in several drawbacks, such as hysteretic behavior, longer response time and deactivation of the Pd. In addition, environmental changes (such as humidity and temperature variations) will also induce unpredictable inaccuracy in the measurement results.

To overcome the above limitations, a palladium-gold-alloy coated optical fiber sensing configuration with a highly tilted Bragg grating (TFBG) inscribed in the fiber core is proposed. The grating tilt within the fiber core has the effect of locally breaking the cylindrical symmetry of the fiber in a way that allows strong coupling between the core-guided light and a large number of cladding modes which then interact with the surface plasmon resonance in the conductive coating. A highly tilted Bragg grating (with a tilt angle bigger than about 35 degrees) can excite a spectral comb of narrowband cladding modes with effective indices near 1.0, which makes them suitable for refractive index measurement in gases. Another key point of this sensor is that by using a palladium-gold alloy nanocoating (rather than pure palladium coating as previously reported), a shorter stabilization time during the association and dissociation phases (less than 20 seconds and 30 seconds, respectively) and improved deactivation resistance (higher than 99% per test cycle) for in situ hydrogen measurement is achieved. Additionally, the sensor provides a self-calibration ability to alleviate the temperature cross-sensitivity: the light remaining in the core of the fiber (the "Bragg resonance") is inherently insensitive to refractive index changes external to the fiber, apart from temperature and strain. Strain effects can be eliminated by suitable packaging while temperature effects can be calibrated out by use of the Bragg resonance as a thermometer (a widely used application of traditional fiber Bragg gratings). In the following parts, a detailed analysis of the operating principle, and the fabrication and the sensing characteristics of the fiber-optic hydrogen sensor using a TFBG and Pd—Au alloy nanocoating, is provided so as to demonstrate its potential as a promising method for rapid, repeatable and highly sensitive hydrogen gas detection.

Materials and Methods

Figures 7A, 7B:
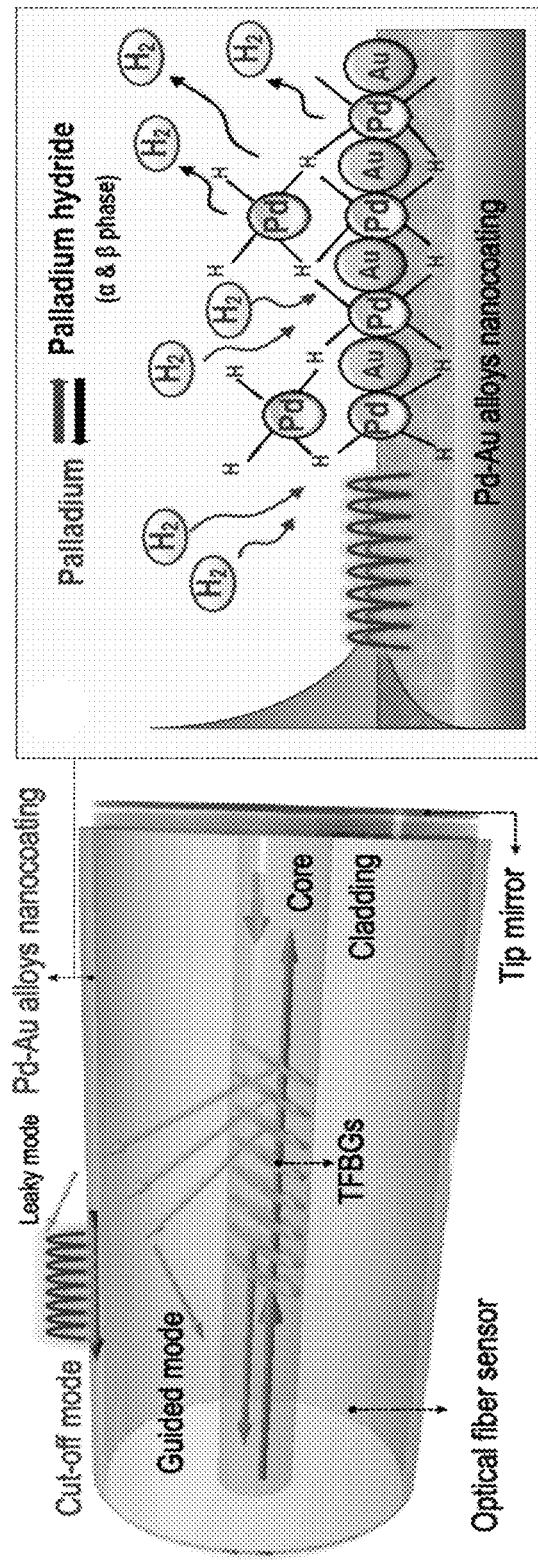
FIG. 7A shows the cut-off surface resonance sensing principle and experimental demonstration with a palladium-gold alloy coated optical fiber sensor with a tilted fiber Bragg grating (TFBG) in the fiber core.
FIG. 7B illustrates a sketch of hydrogen-induced phase transition from metal state to metal hydride state over palladium-gold alloy nanocoating.

Fabrication of TFBG: The optical structure proposed here is shown in FIGS. 7A and 7B. The 16 mm long TFBG sensor was manufactured using the phase-mask technique in a commercial single-mode fiber. The fabrication process of TFBG has been clearly described in. The tilt angle of the grating is an important parameter that can be used to choose which set of cladding modes is to be excited. As a result, it is possible for us to adjust the operating range of the sensor in order to optimize the sensor's response for the desired range of refractive indices. Here, the tilt angle of TFBG was selected to be 37°, which maximizes the cladding mode amplitudes for gaseous measurement, with a surrounding refractive index in the range of 0.9 to 1.1.

Pd—Au alloy nanocoating: A Pd—Au alloy film was deposited on the fiber probe by sputtering. To achieve a high-quality coating, three issues must be addressed. Firstly, to improve the film's adhesion, here we use a 2-3 nm thickness of chromium sandwiched between the optical fiber surface and the Pd—Au alloy film. Secondly, Pd and Au targets are simultaneously sputtered using a single common radio-frequency power source to make sure of forming one single-layer and uniformly-mixed nanocoating over optical fiber. Thirdly, we need to ensure a uniform thickness of Pd—Au alloy film is sputtered over the whole fiber surface. The traditional flat-plane sputtering technique is not well matched to the small-diameter cylindrical fiber because sputtering is directional from the fixed target. To avoid azimuthal thickness nonuniformities, during the sputtering process the fiber was rotated about its axis. With this design, we can ensure a very uniform nanometric coating over the fiber surface. In this case, a high-quality Pd—Au alloy nanocoating with a concentration of 56% Au, and a thickness of 50 nm has been deposited on the surface of the TFBGs.

Figure 8:
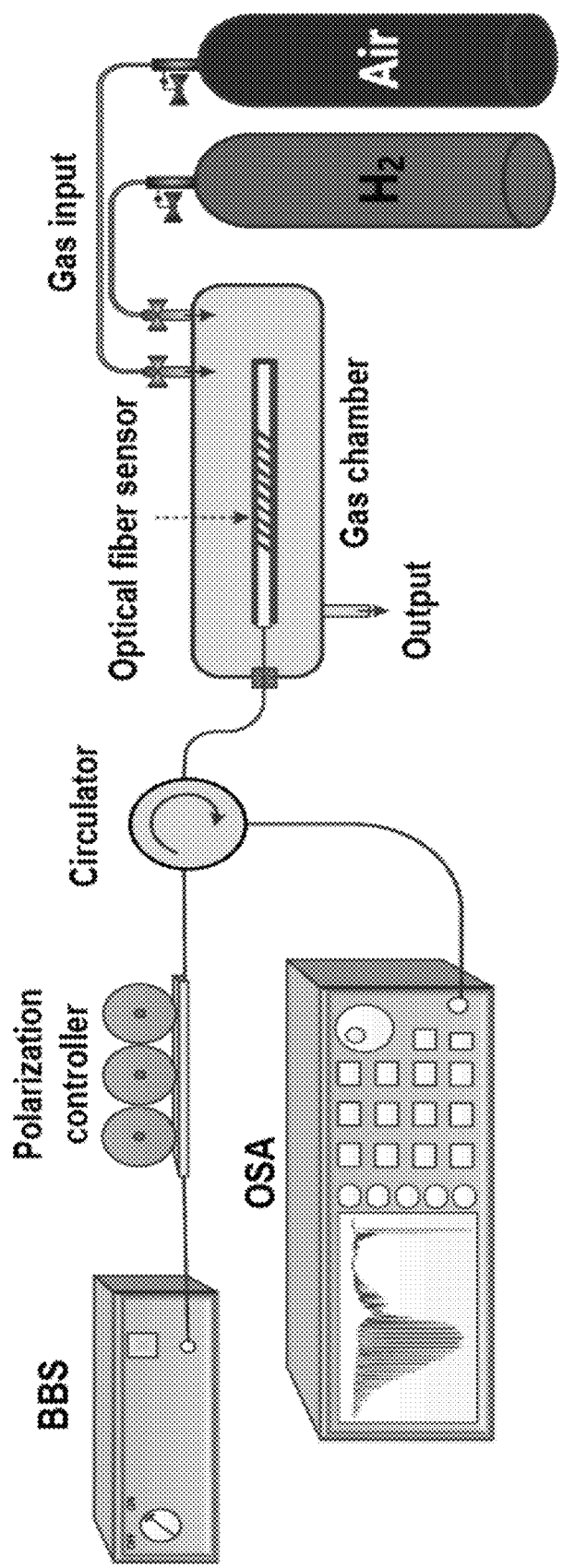
FIG. 8 illustrates the setup used to evaluate the sensing characteristics of the sensor in the presence of hydrogen.

Experiment setup: The performance of the sensor for hydrogen detection was evaluated by introducing the optical fiber probe into a gas chamber and using the setup illustrated in FIG. 8. A broadband light source (BBS) emitting over a wavelength range of 1250-1650 nm was connected to a polarization controller in order to select a suitable polarization, and finally, the interrogation was carried out with an optical spectrum analyzer (OSA). The gas chamber incorporated two gas inlets, i.e. hydrogen ($H_2$) and air. By controlling the flow of each of the gases, different hydrogen concentrations could be achieved with rapid concentration switching.

Figure 9A:
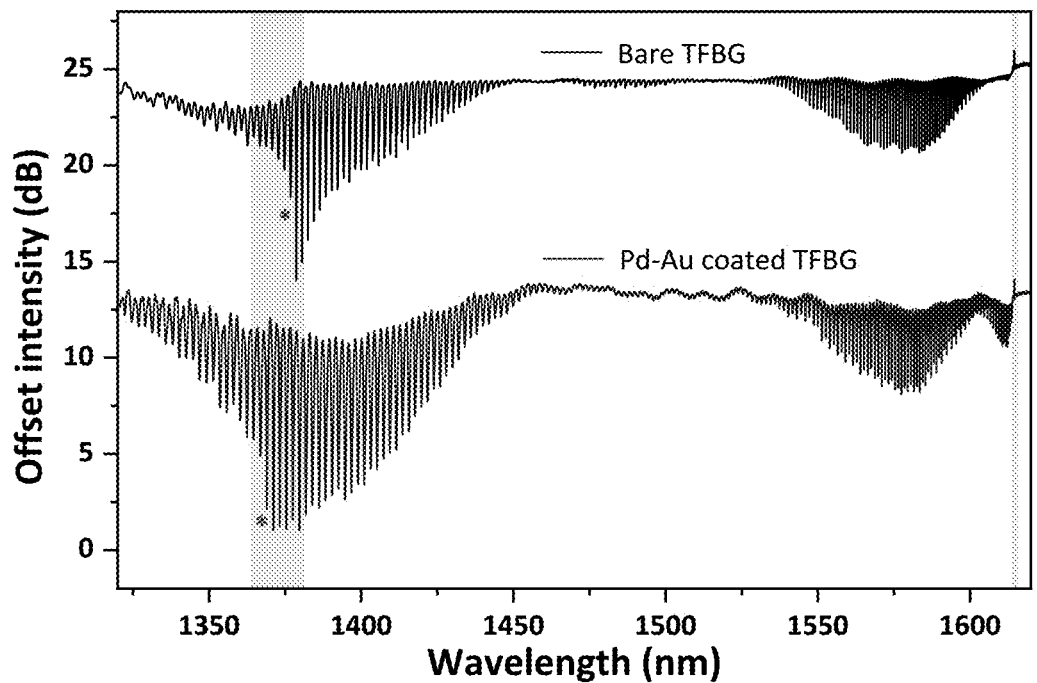
FIG. 9A shows the transmitted amplitude spectra of 37° tilt fiber Bragg grating bare TFBGs in air and Pd—Au alloy nanocoated TFBG in the presence of 2% hydrogen and air respectively.
Figure 9B:
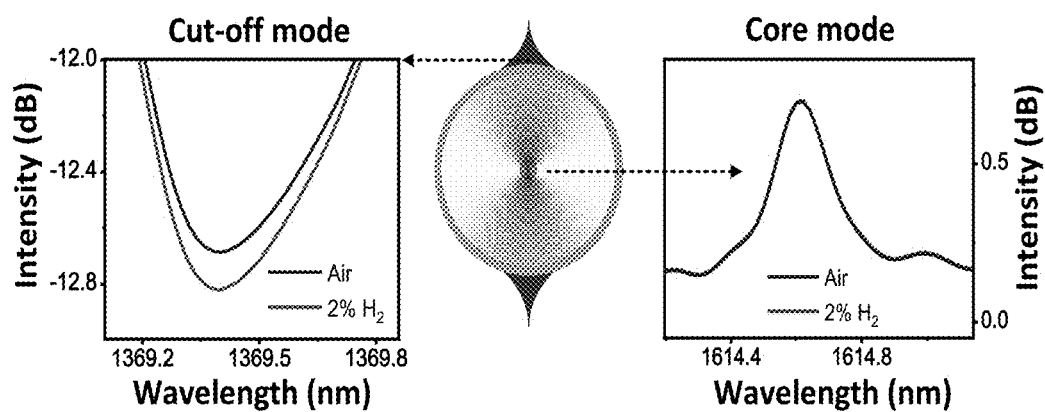
FIG. 9B shows the enlarged detail of the cut-off surface mode resonance (left panel) when sensor is exposed to pure air to air with 2% hydrogen and a schematic cross-section of cut-off mode's optical field distribution for the Pd—Au alloy nanocoated TFBG, and also shows the core mode (right panel) used as a temperature reference.

Sensing methods: It is well known that the TFBG structure can couple the incident core mode into the reflected core mode and a large number of reflected cladding modes. The guided cladding modes have an effective refractive index (ERI) higher than the surrounding refractive index (SRI), and are thus totally internally reflected inside the fiber, while the leaky cladding modes, whose ERI is less than the SRI, will be cut off. The cut-off mode resonance shown by the red asterisk marked on the black curve of FIGS. 9A and 9B, is the mode whose evanescent field extends furthest from the cladding and consequently exhibits the maximum sensitivity to SRI. If no actual cladding mode has an ERI equal to the SRI, the boundary between guided and leaky modes is called the "cut-off condition" and the closest guided mode on the long wavelength side is the mode with the greatest evanescent field penetration into the external medium and hence the largest sensitivity. The boundary between guided and leaky modes is indicated by a sudden increase in the loss of the modes, evidenced by a sharply reduced amplitude of the cladding mode resonances. The operating point (i.e., the range of wavelengths where modes have maximum sensitivity, near the "cut-off condition" for instance) determines the choice of tilt angle: increasing the tilt angle shifts the maximum of the resonance amplitudes towards lower wavelengths. In this work, we track a cut-off surface resonance. Unlike other fiber Bragg grating (FBG) based hydrogen sensors which exploit the swelling of a Pd film as it becomes loaded with hydrogen, in our work we exploit the optical response of this sensor as the metal coating converts from pure Pd to Pd hydride in the presence of hydrogen gas. This scheme offers outstanding sensing characteristics for rapid hydrogen detection and is high resistant to deactivation.

FIG. 9A depicts the transmitted optical spectra of a 37° TFBG (in which the internal tilt angle was 23°, and this angle difference is original from the refractive index difference between the fiber cladding (~1.445) and outside air (~1.002)) with and without Pd—Au alloy coating surrounded by air. The cladding mode resonances at the shorter wavelength side of the core mode (Bragg resonance) can be divided into two main subsets: one group of cladding modes, in the wavelength range of 1530-1612 nm, has effective refractive indices ranging from 1.30 to 1.44. Therefore, this group of cladding modes is suited for measurement in aqueous solutions. The other group of cladding modes, in the wavelength range of 1320-1450 nm, has effective refractive indices ranging from 0.92 to 1.18, constitutes the key elements of cladding modes with a phase-matching condition to the air and the specific gas to be measured.

The red asterisk remarked in the blue curve of FIG. 9A indicates the position of the cut-off wavelength in the air, corresponding to the cladding mode resonance for which its effective refractive index matches the surrounding refractive index of the medium. Resonances at wavelengths shorter than the cut-off wavelength belong to the class of leaky cladding modes.

When we observe the cut-off resonance (near the red asterisk in FIG. 9A, and in the expanded view in FIG. 9B)

we note a marked change in its amplitude according to whether the surrounding gas is pure air (blue curve in FIG. 9B) or air with 2% hydrogen gas added (red curve in FIG. 9B). It should be noted that the expected refractive index difference in the gas should be only at the level of $10^{-6}$ to $10^{-7}$ MU. Therefore, the strong change in amplitude of cut-off resonance must mainly originate from the effective refractive index modulation of the Pd—Au alloy film covering the fiber surface, which is essentially due to the insertion of atomic hydrogen into the Pd crystal lattice and the consequently induced reversible phase transition of Pd—Au alloy from a metal to a metal hydride state, as shown in FIG. 7B. At room temperature, less than 2% $H_2$ concentration range corresponds to the beginning of the transition of the PdHx compound from the so-called "alpha phase" to "beta phase". The alpha phase corresponds to a state where the $H_2$ is just physically dissolved into the Pd matrix but does not chemically bond to the palladium. The beta phase corresponds to chemically stable palladium hydride. Also shown in FIG. 9B, the core mode (the Bragg resonance, shown in the right panel of the figure) at the longest wavelength of 1614.5 nm, remains virtually unchanged, confirming that the change of the cut-off mode arises from surrounding refractive index changes of the gas media and not from physical effects such as strain or temperature. Any unwanted temperature and power level fluctuation effects can, therefore, be subtracted from the sensor response.

Results and Discussion

Improved Sensing Characteristics

Figure 10:
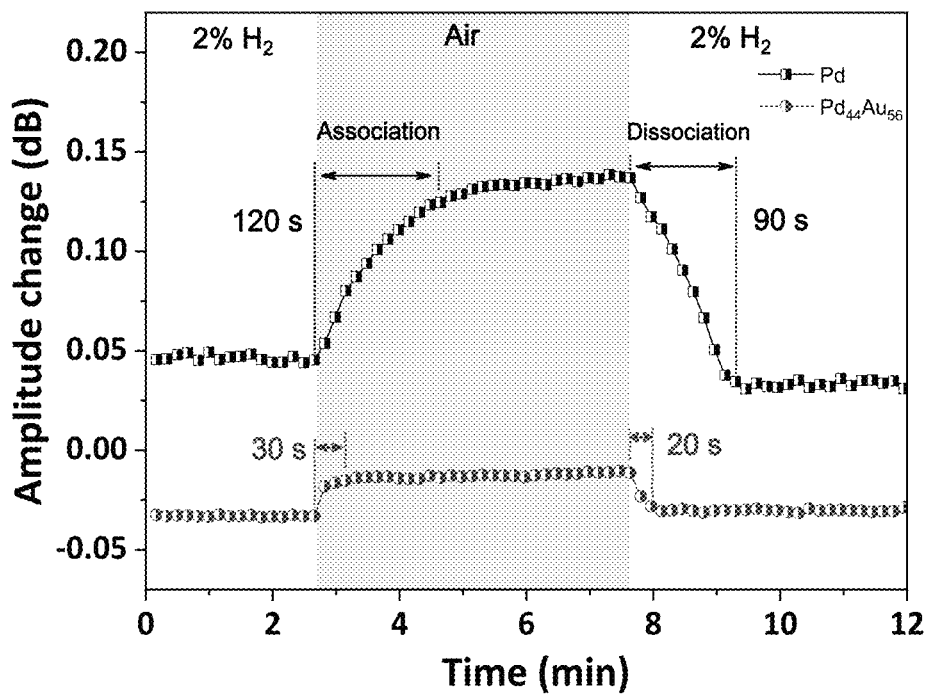
FIG. 10 shows the sensor's response time for hydrogen detection with pure Pd and Pd—Au alloy nanocoatings.

FIG. 10 shows the real-time optical response of the fiber-optic sensor to hydrogen with two different nanocoatings: pure Pd and Pd—Au alloy, respectively. The hydrogen concentration is 2% in the air (lower than the explosive concentration of 4%) and is abruptly changed to 0% by introducing airflow. Compared to the pure Pd coating, the stabilization time during the association phase has been greatly reduced from 90 seconds to 20 seconds by using Pd—Au alloy. Meanwhile, the stabilization time during the dissociation phase has also been decreased from 120 seconds to 30 seconds. This is because the absorbed hydrogen occupies the octahedral interstices of the Pd lattice in both the α- and β-phase hydrides, but because of the limited hydrogen content at room temperature, the sites are not all occupied. The Pd—Au alloy has greater α-phase solubility than pure Pd. Thus the stabilization times during the association and dissociation phases are faster.

Figure 11:
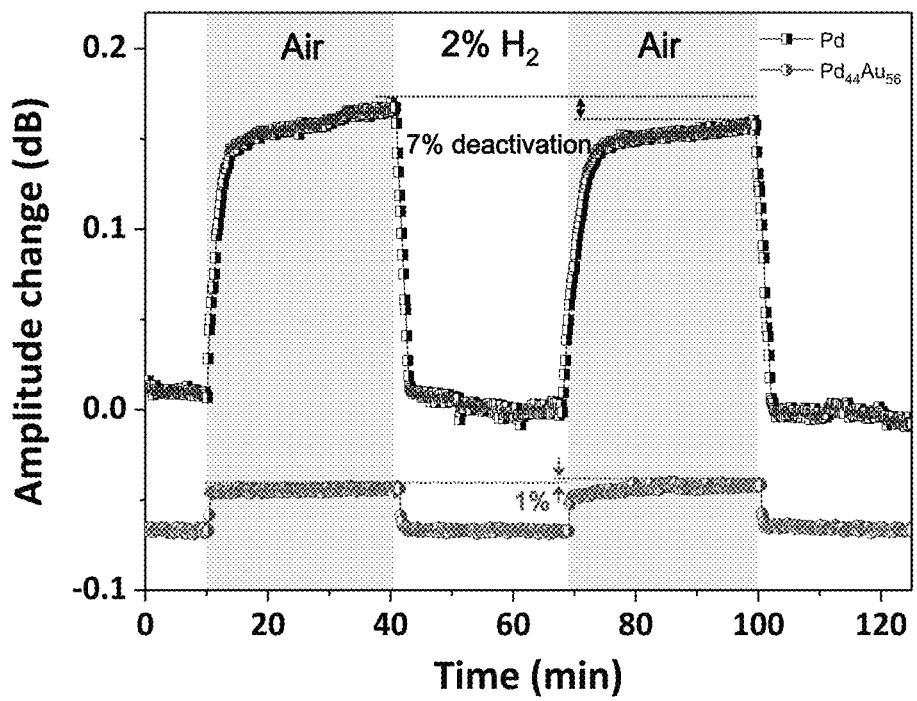
FIG. 11 shows the sensor's repeatability in the hydrogen cycling detection with pure Pd and Pd—Au alloy nanocoatings, respectively.

FIG. 11 shows a response of the sensor for detecting repetitive hydrogen concentration cycling between 0% and 2% $H_2$ by volume concentration in air. The relative optical amplitude changes are higher when the fiber sensor coated with pure Pd than with the Pd—Au alloy. However, the signal-noise-ratio of the fiber sensor with pure Pd is lower than that of the Pd—Au alloy coating, because of the stronger fluctuations over the 2% $H_2$ testing period. More importantly, the repeatability of the sensor for hydrogen cycling detection has been significantly improved by using the Pd—Au alloy nanocoating. As the dash-dot-lines marked in FIG. 11, a strong hydrogen deactivation of 7% has been founded in the pure Pd nanocoated sensor while there is less than 1% deactivation in the Pd—Au alloy nanocoating. This is because the surface of the Pd—Au alloy was much more resistant to hydrogen-induced deformation for the above test cycle than pure Pd was.

Figure 12A:
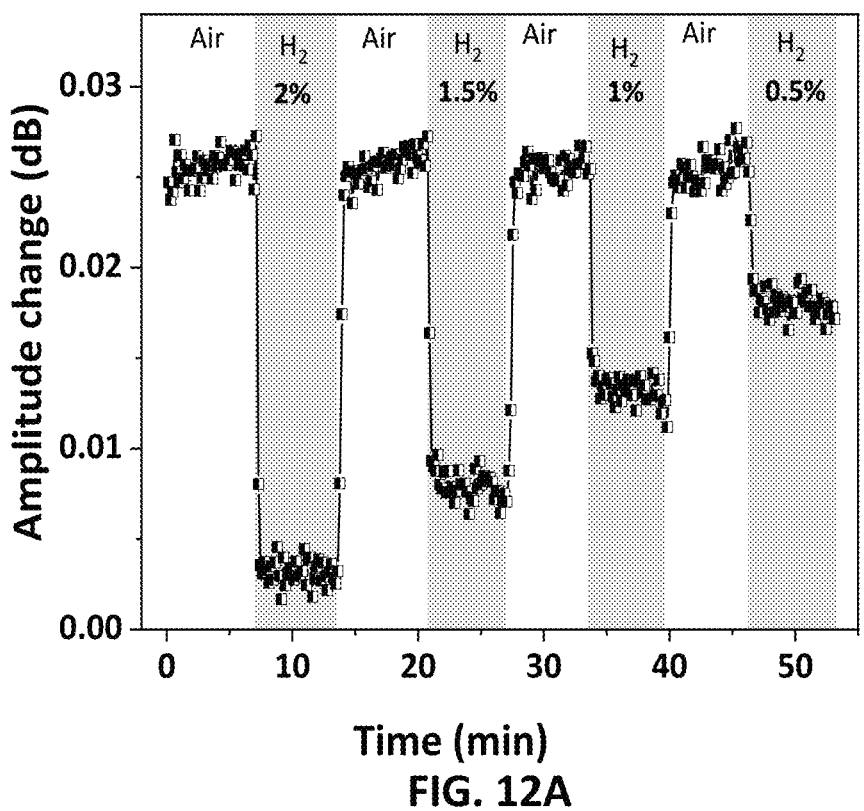
FIGS. 12A and 12B respectively show the response of the sensor to the presence of hydrogen with the concentration range from 0-2% in volume, and the linear response of the sensor.
Figure 12B:
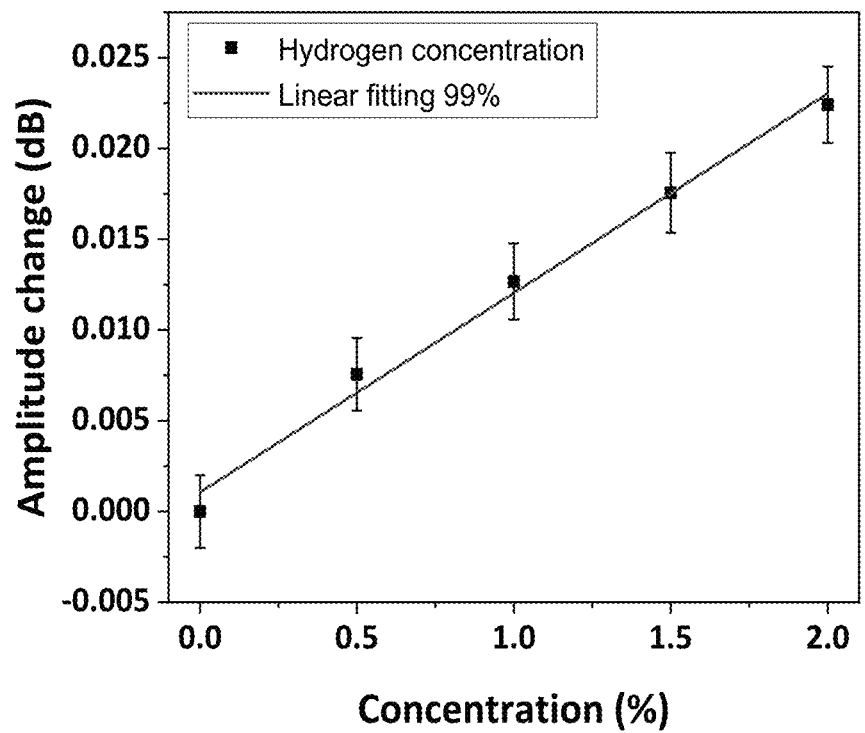

FIG. 12A presents the response of the Pd—Au alloy nanocoated sensor to the presence of different concentrations hydrogen. The sensor exhibits excellent reversibility. As can be seen, the sensor reacts to hydrogen concentrations by volume of 0.5%, 1%, 1.5%, and 2%, all of which are way below the lower explosive limit of the gas, which corresponds to a concentration of 4%. The linear response with correlation coefficient of 99% is obtained using our sensor at concentrations in air from 0 to 2% as can be seen in FIG. 12B. Long time and constant hydrogen concentration detection show that the average standard deviation of the optical intensity of the cut-off mode was 0.002 dB. Thus we may estimate the limit of detection (LOD) of our sensor is about 2300 ppm. The LOD is mainly limited by the slight fluctuation of the broadband light source (especially around 1370 nm, where the cut-off mode was monitored). This problem can be definitely solved by using a real-time interrogation scheme based on power measurement in a narrow band of the optical spectrum. In this case, a tunable laser (TLS) could be used as a source instead of a broadband source, together with a photodiode (PD) as a detector and an analog-to-digital converter (A/D) to obtain the desired data (to replace the optical spectrum analyzer). The function of the TLS is to probe the transmission at the wavelength of the most sensitive mode of the fiber grating (in this case the cut-off mode), determined by initial calibration with a spectrum analyzer. This technique relies on the principle of edge filtering so that the optical power change is produced as a result of the wavelength shift of the mode with respect to the fixed wavelength of the laser source.

Figure 13A:
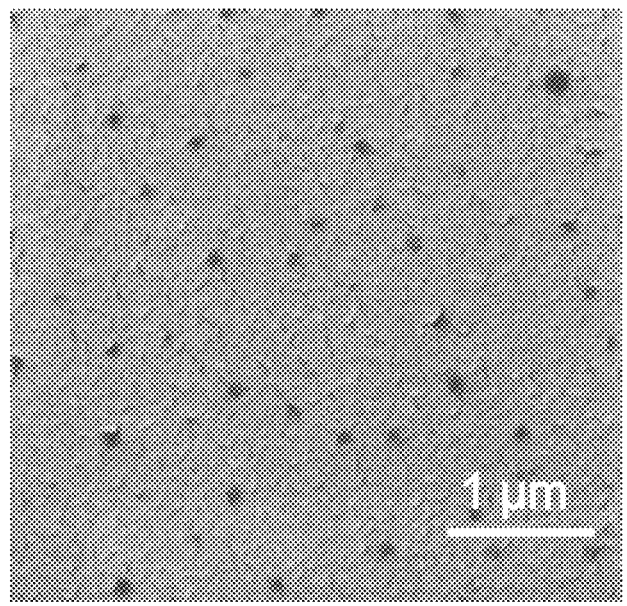
FIGS. 13A and 13B respectively show the morphology of the nanocoatings of pure Pd and Pd—Au alloy after the sensor is exposed to the presence of the hydrogen.
Figure 13B:
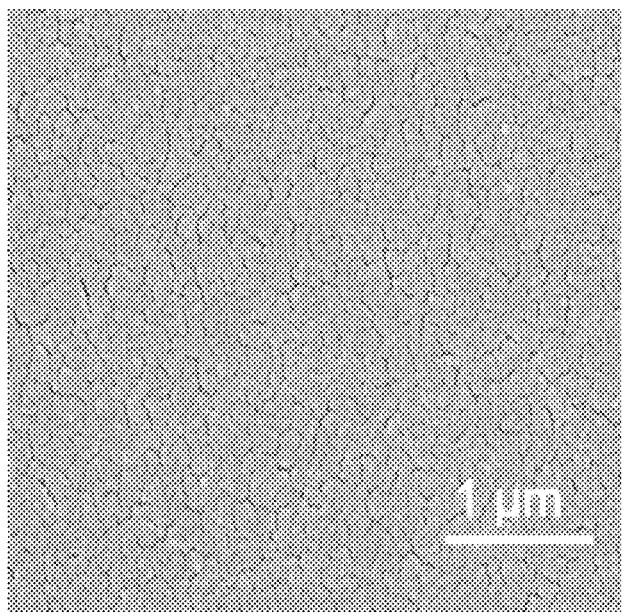

The surface morphology of pure Pd and Pd—Au alloy was examined after hydrogen cycling detection, as shown in the SEM images illustrated in FIGS. 13A and 13B. The images were obtained using a Leica stereo scan 440 scanning electron microscope (SEM). There are some cracks on the surface of the pure Pd and Pd—Au alloy after exposure to the hydrogen environment. Most of those cracks are caused by the process of magnetron sputtering when the pure Pd and the Pd—Au alloy were deposited on the surface of the fiber. But in the case of pure coating Pd as shown in FIG. 13A, much larger pore structures are seen over the surface after the sensor is exposed to the environment of 2% hydrogen, while the Pd—Au alloy surface, as can be seen in FIG. 13B is smoother with small, dense cracks. The result indicates that the Pd hydride is well protected by the Pd—Au alloy shell. As the SEM image in FIG. 13A shows, the pure Pd hydride is more susceptible to deformation during the process of hydrogen-induced phase transition. This problem could be highly suppressed by using Pd—Au alloy.

CONCLUSIONS

The cut-off surface resonance sensing principle based on palladium-gold alloy nanocoated optical fiber sensor with a TFBG in the fiber core has been proposed and experimentally demonstrated. The cut-off mode resonance has the largest evanescent mode extent of any mode, and therefore exhibits the maximum sensitivity for the TFBG sensor. A faster response time (stabilization time during the association and dissociation phases are less than 20 and 30 seconds, respectively) and an improved deactivation resistance has been achieved for specific hydrogen measurement. We believe that this configuration opens research directions for rapid, repeatable and highly effective resistance to deactivation in hydrogen gas. Together with the intrinsic features of optical fibers, these sensors provide a promising platform for hydrogen detection under harsh conditions, like the implantation of the sensor into a hydrogen-fuel cell for in situ renewable energy vehicle monitoring.

The contents of all references, as cited throughout the disclosure, are incorporated in their entirety by reference.

REFERENCES

T. Shujah, M. Ikram, A. R. Butt, M. K. Shahzad, K. Rashid, Q. Zafar, and S. Ali, "H$_2$S Gas Sensor Based on WO3 Nanostructures Synthesized via Aerosol Assisted Chemical Vapor Deposition Technique," Nanoscience and Nanotechnology Letters 11(9), 1247-1256 (2019).

S. Singh, N. Dogra, and S. Sharma, "A sensitive H2S sensor using MoS2/WO3 composite," Materials Today: Proceedings (2020).

L. Yin, G. Qu, P. Guo, R. Zhang, J. Sun, and D. Chen, "Construction and enhanced low-temperature H2S-sensing performance of novel hierarchical CuO@ WO3 nanocomposites," Journal of Alloys and Compounds 785, 367-373 (2019).

K. Bunpang, A. Wisitsoraat, A. Tuantranont, S. Singkammo, S. Phanichphant, and C. Liewhiran, "Highly selective and sensitive CH4 gas sensors based on flame-spray-made Cr-doped SnO2 particulate films," Sensors-Actuators B: Chemical 291, 177-191 (2019).

A. Das and D. Panda, "SnO2 Tailored by CuO for Improved CH4 Sensing at Low Temperature," physica status solidi (b) 256(5), 1800296 (2019).

Y. H. Navale, S. T. Navale, F. J. Stadler, N. S. Ramgir, and V. B. Patil, "Enhanced NO$_2$ sensing aptness of ZnO nanowire/CuO nanoparticle heterostructure-based gas sensors," Ceramics International 45(2), 1513-1522 (2019).

G. Cai, P. Duan, J. Cong, C. Zhang, Y. Zheng, F. Zhong, Y. Xiao, and L. Jiang, "Cu incorporated perovskite Na0. 5Bi0. 5TiO3 oxygen-defect conductor as NO2 sensor using CuO sensitive electrode," Ceramics International 45(7), 8494-8503 (2019).

L. Zhang, X. Cheng, G. Zhang, W. Qiu, H. He, and G. Chen, "High Active Platinum Clusters on Titanium Dioxide Supports toward Carbon Monoxide Oxidation," Applied Catalysis B: Environmental 118629 (2020).

S. A. M. Chachuli, M. N. Hamidon, M. Ertugrul, M. S. Mamat, H. Jaafar, and N. H. Shamsudin, "TiO2/B2O3 thick film gas sensor for monitoring carbon monoxide at different operating temperatures," in Journal of Physics: Conference Series (IOP Publishing, 2020), 1432(1), p. 012040.

N. D. Chinh, T. T. Hien, L. Do Van, N. M. Hieu, N. D. Quang, S.-M. Lee, C. Kim, and D. Kim, "Adsorption/desorption kinetics of nitric oxide on zinc oxide nano film sensor enhanced by light irradiation and gold-nanoparticles decoration," Sensors and Actuators B: Chemical 281, 262-272 (2019).

P. Singh, L.-L. Hu, H.-W. Zan, and T.-Y. Tseng, "Highly sensitive nitric oxide gas sensor based on ZnO-nanorods vertical resistor operated at room temperature," Nanotechnology 30(9), 095501 (2019).

J. Sun, L. Sun, S. Bai, H. Fu, J. Guo, Y. Feng, R. Luo, D. Li, and A. Chen, "Pyrolyzing Co/Zn bimetallic organic framework to form pn heterojunction of Co3O4/ZnO for detection of formaldehyde," Sensors and Actuators B: Chemical 285, 291-301 (2019).

M. H. Jali, H. R. A. Rahim, M. A. M. Johari, H. H. M. Yusof, B. M. A. Rahman, S. W. Harun, and M. Yasin, "Formaldehyde sensing using ZnO nanorods coated glass integrated with microfiber," Optics & Laser Technology 120, 105750 (2019).

K. Khamfoo, K. Inyawilert, A. Wisitsoraat, A. Tuantranont, S. Phanichphant, and C. Liewhiran, "Formaldehyde sensor based on FSP-made AgOx-doped SnO2 nanoparticulate sensing films," Sensors and Actuators B: Chemical 127705 (2020).

G. Li, Z. Cheng, Q. Xiang, L. Yan, X. Wang, and J. Xu, "Bimetal PdAu decorated SnO2 nanosheets based gas sensor with temperature-dependent dual selectivity for detecting formaldehyde and acetone," Sensors and Actuators B: Chemical 283, 590-601 (2019).

W. Guo, Q. Zhou, J. Zhang, M. Fu, N. Radacsi, and Y. Li, "Hydrothermal synthesis of Bi-doped SnO2/rGO nanocomposites and the enhanced gas sensing performance to benzene," Sensors and Actuators B: Chemical 299, 126959 (2019).

E. Grinenval, F. James, D. Porterat, F. Abedini, M.-P. Som, T.-H. Tran-Thi, and M. Mayne-L'hermite, "Chemical sensor based on carbon nanotube combined to a preconcentrator nanoporous layer for the detection of benzene," in (2019).

The invention claimed is:

1. A sensing apparatus for selectively detecting at least one target molecule in a gaseous medium, comprising an optical fiber and a coating assembly coating an outer surface of the optical fiber, wherein:
   the optical fiber comprises a core and a cladding surrounding the core, wherein the core is provided with a tilted grating, configured to generate surface plasmon waves at an interface between the coating assembly and the gaseous medium upon a compatible electromagnetic radiation propagating in the optical fiber; and
   the coating assembly comprises a composite film layer having an outer surface in direct contact with the gaseous medium, wherein:
      the composite film layer comprises at least two compositions mixed with one another therein, wherein:
         the at least two compositions comprise one or more active compositions, each configured to be active to surface plasmon resonance (SPR); and
         the at least two compositions comprise one or more reacting compositions, each configured to be reversibly reactive to one or more of the at least one target molecule.

2. The sensing apparatus of claim 1, wherein the one or more active compositions in the composite film layer comprise at least one of gold (Au), silver (Ag), platinum (Pt), aluminum (Al), or copper (Cu).

3. The sensing apparatus of claim 1, wherein the one or more reacting compositions in the composite film layer comprise at least one of palladium (Pd), metallic La—Mg$_2$—Ni, tungsten trioxide (WO$_3$), carbon nanotubes (CNT), Si nanowires, tin dioxide (SnO$_2$), a metal-polymer hybrid nanomaterial, a semiconductor oxide nanostructure, a core/shell plasmonic nanorod metamaterial, zinc oxide (ZnO), titanium oxide (TiO$_2$), iron oxide (Fe$_2$O$_3$/Fe$_3$O$_4$), polyaniline, polypyrrole, metal phthalocyanine, graphite oxide, or copper (II) oxide (CuO).

4. The sensing apparatus of claim 3, wherein the one or more reacting compositions in the composite film layer comprise at least one of palladium (Pd), metallic La—Mg$_2$—Ni, Si nanowires, a metal-polymer hybrid nanomaterial, a semiconductor oxide nanostructure, a core/shell plasmonic nanorod metamaterial, and the at least one target molecule comprises hydrogen (H$_2$).

5. The sensing apparatus of claim 4, wherein the one or more reacting compositions comprise palladium (Pd), having a weight concentration of approximately 20%-80% in the composite film layer.

6. The sensing apparatus of claim 5, wherein the one or more active compositions in the composite film layer comprise gold (Au).

7. The sensing apparatus of claim 3, wherein:
the one or more reacting compositions comprise $WO_3$, and the at least one target molecule comprises at least one of hydrogen ($H_2$), $H_2S$, or ammonia ($NH_3$);
the one or more reacting compositions comprise $SnO_2$, and the at least one target molecule comprises at least one of hydrogen ($H_2$), $CH_4$, formaldehyde, benzene, or ammonia ($NH_3$);
the one or more reacting compositions comprise CuO, and the at least one target molecule comprises $NO_2$;
the one or more reacting compositions comprise $TiO_2$, and the at least one target molecule comprises at least one of CO or ammonia ($NH_3$);
the one or more reacting compositions comprise ZnO, and the at least one target molecule comprises at least one of NO, formaldehyde, or ammonia ($NH_3$);
the one or more reacting compositions comprise carbon nanotubes, and the at least one target molecule comprises hydrogen ($H_2$), benzene; or
the one or more reacting compositions comprise at least one of iron oxide ($Fe_2O_3/Fe_3O_4$), polyaniline, polypyrrole, or metal phthalocyanines, and the at least one target molecule comprises ammonia ($NH_3$).

8. The sensing apparatus of claim 1, wherein the composite film layer has a thickness in range of approximately 25-75 nm.

9. The sensing apparatus of claim 1, wherein an internal tilt angle of the tilted grating is at least approximately 20 degrees.

10. The sensing apparatus of claim 1, wherein the coating assembly further comprises a transition layer, sandwiched between the outer surface of the optical fiber and an inner surface of the composite film layer, wherein the transition layer is configured to improve adhesion of the composite film layer to the optical fiber, wherein the transition layer comprises at least one of titanium (Ti), molybdenum (Mo), or chromium (Cr).

11. The sensing apparatus of claim 1, wherein the coating assembly further comprises a substrate layer, sandwiched between the outer surface of the optical fiber and an inner surface of the composite film layer, wherein the substrate layer is configured to be active to SPR and comprises at least one of gold (Au), silver (Ag), platinum (Pt), aluminum (Al), or copper (Cu).

12. The sensing apparatus of claim 11, wherein the coating assembly further comprises a transition layer, sandwiched between the outer surface of the optical fiber and an inner surface of the substrate layer, wherein the transition layer is configured to improve adhesion of the substrate layer to the optical fiber, wherein the transition layer comprises at least one of titanium (Ti), molybdenum (Mo), or chromium (Cr).

13. A sensing system, comprising:
the sensing apparatus according to claim 1;
a light source apparatus, optically coupled to a first end of, and configured to provide an input light into, the sensing apparatus so as to allow the electromagnetic radiation to propagate in the core of the optical fiber of the sensing apparatus; and
a signal detection apparatus, coupled to the sensing apparatus and configured to obtain the signals of the surface plasmon waves therefrom so as to derive the information of the at least one target molecule in the gaseous medium.

14. The sensing system of claim 13, wherein:
the light source apparatus comprises a broadband source (BBS), and the signal detection apparatus comprises an optical spectrum analyzer (OSA); or
the light source comprises a tunable laser source (TLS), and the signal detection apparatus comprises:
an optical detector, configured to detect, and to convert into analog electrical signals, the signals of the plasmon waves from the sensing apparatus; and
an analog-to-digital converter, configured to convert the analog electrical signals into digital electrical signals.

15. The sensing system of claim 13, wherein the signal detection apparatus is coupled to the first end of the optical fiber, wherein:
a second end of the optical fiber is provided with a mirror having a reflection surface facing to, configured to reflect the electromagnetic radiation back towards, the first end of the optical fiber; and
the sensing system further comprises a coupler, wherein:
the coupler is arranged between the light source apparatus and the sensing apparatus along an input optical pathway and between the sensing apparatus and the signal detection apparatus along an output optical pathway; and
the coupler is configured to separate the input optical pathway and the output optical pathway to thereby allow the signal detection apparatus to obtain the signals of the surface plasmon waves from the sensing apparatus without being influenced by the input light.

16. A method for manufacturing a sensing apparatus capable of selectively detecting at least one target molecule in a gaseous medium, comprising:
providing an optical fiber, wherein the optical fiber comprises a core and a cladding surrounding the core, and the core is provided with a tilted grating, configured to generate surface plasmon waves at an interface between the coating assembly and the gaseous medium upon a compatible electromagnetic radiation propagating in the optical fiber; and
coating a composite film layer over an outer surface of the optical fiber, wherein the composite film layer comprises at least two compositions mixed with one another therein, wherein:
the at least two compositions comprise one or more active compositions, each configured to be active to surface plasmon resonance (SPR); and
the at least two compositions comprise one or more reacting compositions, each configured to be reversibly reactive to one or more of the at least one target molecule.

17. The method according to claim 16, wherein the coating a composite film layer over an outer surface of the optical fiber is realized by means of sputtering, electroplating, or chemical deposition.

18. The method according to claim 17, wherein the coating a composite film layer over an outer surface of the optical fiber is realized by means of sputtering, and the coating a composite film layer over an outer surface of the optical fiber comprises:

simultaneously sputtering the at least two compositions to the optical fiber while the optical fiber is rotating about an axis thereof.

19. The method according to claim 18, wherein each of the at least two compositions in the composite film layer is a metal, and the simultaneously sputtering the at least two compositions to the optical fiber is by means of a single common radio-frequency power source.

20. The method according to claim 16, further comprising, between the providing an optical fiber and the coating a composite film layer over an outer surface of the optical fiber:

coating a transition layer over an outer surface of the optical fiber;

wherein:

the coating a composite film layer over an outer surface of the optical fiber comprises:

coating a composite film layer over an outer surface of the transition layer.

\* \* \* \* \*